US005677124A

United States Patent [19]
DuBois et al.

[11] Patent Number: 5,677,124
[45] Date of Patent: Oct. 14, 1997

[54] RIBONUCLEASE RESISTANT VIRAL RNA STANDARDS

[75] Inventors: Dwight B. DuBois; Matthew M. Winkler; Brittan L. Pasloske, all of Austin, Tex.

[73] Assignees: Ambion, Inc.; Cenetron Diagnostics LLC, both of Austin, Tex.

[21] Appl. No.: 675,153

[22] Filed: Jul. 3, 1996

[51] Int. Cl.$^6$ .............................. C20Q 1/70; C12M 1/24; C12N 7/01; C12P 19/34
[52] U.S. Cl. .................. 435/5; 435/69.1; 435/235.1; 435/240.1; 435/287.2; 435/288.1; 536/23.1
[58] Field of Search ........................ 435/5, 69.1, 91.1, 435/235.1, 320.1, 287.2, 88.1; 536/23.1

[56] References Cited

U.S. PATENT DOCUMENTS 5,443,969  8/1995  Wilson et al.

FOREIGN PATENT DOCUMENTS

WO87/06261  10/1987  WIPO ........................... C12N 15/00

OTHER PUBLICATIONS

Dolja et al., "Phylogeny of Capsid Proteins of Rod-Shaped and Filamentous RNA Plant Viruses: Two Families with Distinct Patterns of Sequence and Probably Structure Conservation," *Virology*, 184:79–86, 1991.

Duda et al., "Expression of Plasmid-Encoded Structural Proteins Permits Engineering of Bacteriophage T4 Assembly," *Virology*, 179:728–737, 1990.

Durham, "Structures and Roles of the Polymorphic Forms of Tobacco Mosaic Virus Protein," *J. Mol. Biol.*, 67:289–305, 1972.

Durham, "The Cause of Irreversible Polymerisation of Tobacco Mosaic Virus Protein," *FEBS Letters*, 25(1):147–152, 1972.

Fritsch et al., "Specificity of TMV RNA Encapsidation: in vitro Coating of Heterologous RNA by TMV Protein," *Virology*, 56:33–45, 1973.

Gal-On et al., "Nucleotide Sequence of the Zucchini Yellow Mosaic Virus Capsid-Encoding Gene and its Expression in *Escherichia coli*," *Gene* 87:273–277, 1990.

Gallie et al., "In Vivo Uncoating and Efficient Expression of Foreign mRNAs Packaged in TMV-Like Particles," *Science*, 236:1122–1124, 1987.

Gallie et al., "The Effect of Multiple Dispersed Copies of the Origin-of-Assembly Sequence From TMV RNA on the Morphology of Pseudovirus Particles Assembled In Vitro," *Virology*, 158:473–476, 1987.

Gibbs, "Tobamovirus Group," *C.M.I./A.A.B. Descriptions of Plant Viruses*, No. 184, Commonwealth Bureaux and the Association of Applied Biologists, Sep. 1977.

Goelet et al., "Nucleotide Sequence of Tobacco Mosaic Virus RNA," *Proc. Natl. Acad. Sci. USA*, 79:5818–5922, 1982.

Goulden et al., "Structure of Tobraviral Particles: A Model Suggested From Sequence Conservation in Tobraviral and Tobamoviral Coat Proteins," *J. Mol. Biol.*, 227:1–8, 1992.

(List continued on next page.)

*Primary Examiner*—David Guzo
*Assistant Examiner*—William Sandals
*Attorney, Agent, or Firm*—Arnold, White & Durkee

[57] ABSTRACT

The present invention is directed to the process of creating a recombinant nucleic acid standard which is resistant to ribonuclease digestion and is non-infectious. A single strand of recombinant nucleic acid is encapsidated by bacteriophage proteins. The recombinant nucleic acid is a hybrid sequence encoding bacteriophage proteins and a specific non-bacteriophage sequence. A non-bacteriophage RNA sequence can be used as an RNA standard to help quantify the number of RNA molecules in an unknown sample. The recombinant RNA in its packaged form is highly resistant to ribonucleases, insuring that the RNA standard is not compromised by inadvertent ribonuclease contamination. These "ARMORED RNA" standards are ideal as RNA standards for the quantification of RNA viruses such as HIV and HCV from human body fluids such as blood and cerebrospinal fluid.

57 Claims, 2 Drawing Sheets

OTHER PUBLICATIONS

Guilley et al., "Observations Concerning the Sequence of Two Additional Specifically Encapsidated RNA Fragments Originating From the Tobacco–Mosaic–Virus Coat–Protein Cistron," *Eur. J. Biochem.*, 54:145–153, 1975.

Guilley et al., "Sequence of a Specifically Encapsidated RNA Fragment Originating From the Tobacco–Mosaic–Virus Coat–Protein Cistron," *Eur. J. Biochem.*, 54:135–144, 1975.

Guo et al., "sRNa of Phage φ29 of *Bacillus subtilis* Mediates DNA Packaging of φ29 Proheads Assembled in *Escherichia coli*," *Virology*, 185:395–400, 1991.

Harrison, "Pea Early–Browning Virus," *C.M.I./A.A.B. Descriptions of Plant Viruses*, No. 120, Commonwealth Bureaux and the Association of Applied Biologists, Jul. 1973.

Harrison, "Tobacco Rattle Virus," *C.M.I./A.A.B. Description of Plant Viruses*, No. 12, Commonwealth Bureaux and the Association of Applied Biologists, Jun. 1970.

Haynes et al., "Development of a Genetically–Engineered, Candidiate Polio Vaccine Employing the Self–Assembling Properties of the Tobacco Mosaic Virus Coat Protein," *Biotechnology*, 4:637–641, 1986.

Hwang et al., "Expression of Tobacco Mosaic Virus Coat Protein and Assembly of Pseudovirus Particles in *Escherichia coli*," *Proc. Natl. Acad. Sci. USA*, 91:9067–9071, 1994.

Jagadish et al., "Expression of Potyvirus Coat Protein in *Escherichia coli* and Yeast and its Assembly into Virus–Like Particles," *Journal of General Virology*, 72:1543–1550, 1991.

Jupin et al., "Direct Recovery of in vitro Transcripts in a Protected Form Suitable for Prolonged Storage and Shipment at Ambient Temperatures," *Nucleic Acids Research*, 17(2):815, 1989.

Koenig and Lesemann, "Potexvirus Group," *C.M.I./A.A.B. Descriptions of Plant Viruses*, No. 200, Commonwealth Bureaux and the Association of Applied Biologists, Aug. 1978.

Meshi et al., "Nucleotide Sequence of a Cloned cDNA Copy of TMV (Cowpea Strain) RNA, Including the Assembly Origin, the Coat Protein Cistron, and the 3' Non–Coding Region," *Mol. Gen. Genet.*, 184:20–25, 1981.

Olkkonen et al., "In Vitro Assembly of Infectious Nucleocapsids of Bacteriophage φ6: Formation of a Recombinant Double–Stranded RNA Virus," *Proc. Natl. Acad. Sci. USA*, 87:9173–9177, 1990.

Rochon and Siegel, "Chloroplast DNA Transcripts Are Encapsidated by Tobacco Mosaic Virus Coat Protein," *Proc. Natl. Acad. Sci. USA*, 81:1719–1723, 1984.

Rochon et al., "Encapsidation of 18 S rRNA by Tobacco Mosaic Virus Coat Protein," *Virology*, 150:140–148, 1986.

Rosenberg and Studier, "T7 RNA Polymerase Can Direct Expression of Influenza Virus Cap–Binding Protein (PB2) in *Escherichia coli*," *Gene*, 59:191–200, 1987.

Sacher et al., "Hybrid Brome Mosaic Virus RNAs Express and Are Packaged in Tobacco Mosaic Virus Coat Protein *in vivo, Virology*", 167:15–24, 1988.

Schein, "Production of Soluble Recombinant Proteins in Bacteria," *Biotechnology*, 7:1141–1149, 1989.

Shire et al., "Preparation and Properties of Recombinant DNA Derived Tobacco Mosaic Virus Coat Protein," *Biochemistry*, 29:5119–5126, 1990.

Siegel, "Pseudovirions of Tobacco Mosaic Virus," *Virology*, 46:50–59, 1971.

Sleat et al., "Packaging of Recombinant RNA Molecules into Pseudovirus Particles Directed by the Origin–of–Assembly Sequence From Tobacco Mosaic Virus RNA," *Virology*, 155:299–308, 1986.

Sleat et al., "Selective Recovery of Foreign Gene Transcripts as Virus–Like Particles in TMV–Infected Transgenic Tobaccos," *Nucleic Acids Research*, 16(8):3127–3141, 1988.

Studier et al., "Use of T7 RNA Polymerase to Direct Expression of Coned Genes," *Methods in Enzymology*, 185:60–89, 1990.

Sugiyama, "Tobacco Mosaic Viruslike Rods Formed by Mixed Reconstitution Between MS2 Ribonucleic Acid and Tobacco Mosaic Virus Protein," *Virology*, 28(3):488–492, 1966.

Turner and Butler, "Essential Features of the Assembly Origin of Tobacco Mosaic Virus RNA as Studied by Directed Mutagenesis," *Nucleic Acids Research*, 14(23):9299–9242, 1986.

Turner et al., "Assembly of Hybrid RNAs with Tobacco Mosaic Virus Coat Protein. Evidence for Incorporation of Disks in 5'–Elongation Along the Major RNA Tail," *J. Mol. Biol.*, 209:407–422, 1989.

Turner et al., "The Tobacco Mosaic Virus Assembly Origin RNA. Functional Characteristics Defined by Directed Mutagenesis," *J. Mol. Biol.*, 203:531–547, 1988.

Wilson et al., "Effects of the 5'–Leader Sequence of Tobacco Mosaic Virus RNA, or Derivatives Thereof, on Foreign mRNA and Native Viral Gene Expression," *NATO ASI Series, Post–Transcriptional Control of Gene Expression*, vol. H49, McCarthy, J.E.G. and Tuite, M.F., eds., Springer–Verlag, Berlin, Heidelberg, pp. 261–275, 1990.

Zimmern and Hunter, "Point Mutation in the 30–K Open Reading Frame of TMV Implicated in Temperature–Sensitive Assembly and Local Lesion Spreading of Mutant Ni 2519," *The EMBO Journal*, 2(11):1893–1900, 1983.

Zimmern, "An Extended Secondary Structure Model for the TMV Assembly Origin, and its Correlation with Protection Studies and an Assembly Defective Mutant," *The EMBO Journal*, 2(11):1901–1907, 1983.

Zimmern, "The 5' End Group of Tobacco Mosaic Virus RNA is $m^7G^{5'}$ $ppp^{5'}$ Gp," *Nucleic Acids Research*, 2(7):1189–1201, 1975.

Argetsinger and Gussin, "Intact Ribonucleic Acid from Defective Particles of Bacteriophage R17," *J Mol Biol*, 21:421–434, 1966.

Aslanzadeh et al., "Evaluation of PCR and Nested PCR for Laboratory Diagnosis of Hepatitis C Virus Infection," *Mol Cell Probes*, 10:173–178, 1996.

Barlow et al., "Analysis and Genotyping of PCR Products of the Amplicor HIV–1 Kit," *J Virological Methods*, 52:65–74, 1995.

Collins et al., "Preparation and Characterization of RNA Standards for Use in Quantitative Branched DNA Hybridization Assays", *Analytical Biochemistry*, 226:120–129, 1995.

Golmohammadi et al., "The Refined Structure of Bacteriophage MS2 at 2·8 Å Resolution," *J Mol Biol*, 234:620–639, 1993.

Heisenberg, "Formation of Defective Bacteriophage Particles by fr Amber Mutants," *J. Mol. Biol.*, 17:136–144, 1966.

Hughes and Andrew, "Creation of Deletion, Insertion and Substitution Mutations Using a Single Pair of Primers and PCR," *Biotechniques*, 20(2):188–196, 1996.

LeCuyer et al., "Mutants of the Bacteriophage MS2 Coat Protein that Alter its Cooperative Binding," *Biochem*, 34:10600–10606, 1995.

Lim and Peabody, "Mutations that Increase the Affinity of a Translational Repressor for RNA," *Nuc Acids Res*, 22(18):3748–3752, 1994.

Lim et al., "Altering the RNA Binding Specificity of a Translational Repressor," *J Biol Chem*, 269(12):9006–9010, Mar. 1994.

Lu and Andrieu, "Use of the Human Immunodeficiency Virus Virion as a Universal Standard for Viral RNA Quantitation by Reverse Transcription–Linked Polymerase Chain Reaction," *J. Infect Diseases*, 167:1499–1500, 1993.

Mastico et al., "Multiple Presentation of Foreign Peptides on the Surface of an RNA–Free Sphereical Bacteriophage Capsid," *J General Virology*, 74:541–548, 1993.

Mellors et al., "Prognosis in HIV–1 Infection Predicted by the Quantity of Virus in Plasma," *Science*, 272:1167–1170, May 1996.

Mulder et al., "Rapid and Simple PCR Assay for Quantitation of Human Immunodeficiency Virus Type 1 RNA in Plasma: Application in Acute Retroviral Infection," *J Clin Microbiol*, 32(2):292–300, Feb. 1994.

Pachl et al., "Rapid and Precise Quantification of HIV–1 RNA in Plasma Using a Branched DNA Signal Amplification Assay," *J Acquired Immune Deficiency Syndromes and Human Retrovirology*, 8:446–454, 1995.

Peabody and Ely, "Control of Translational Repression by Protein–Protein Interactions," *Nuc Acids Res*, 20(7):1649–1655, 1992.

Peabody and Lim, "Complementation of RNA Binding Site Mutations in MS2 Coat Protein Heterodimers," *Nuc Acids Res*, 24(12):2352–2359, 1996.

Peabody, "Translational Repression by Bacteriophage MS2 Coat Protein Expressed from a Plasmid," *J Biol Chem*, 265(10):5684–5689, Apr. 1990.

Piatek et al., "*Quantitative Competitive Polymerase Chain Reaction for Accurate Quantitation of HIV DNA and RNA Species,*" *Biotechniques*, 14(1):70–79, 1993.

Pickett and Peabody, "Encapsidation of Heterologous RNAs by Bacteriophage MS2 Coat Protein," *Nuc Acids Res*, 21(19):4621–4626, 1993.

Pushko et al., "Analysis of RNA Phage fr Coat Protein Assembly by Insertion, Deletion and Substitution Mutagenesis," *Protein Engineering*, 6(8):883–891, 1993.

Qiao et al., "Interference with Bacteriophage φ6 Genomic RNA Packaging by Hairpin Structures," *J Virology*, 69(9):5502–5505, Sep. 1995.

Schneeberger and Zeillinger, "PCR–Mediated Synthesis of Exogenous Competitors for Quantitative RT–PCR," *Biotechniques*, 20(3):360–361, 1996.

Shaklee et al., "Infectious Positive– and Negative–Strand Transcript RNAs from Bacteriophage Qβ cDNA Clone," *Virology*, 163:209–213, 1988.

Shaklee, "Negative–Strand RNA Replication by Qβ and MS2 Positive–Strand RNA Phage Replicases," *Virology*, 178:340–343, 1990.

Shiba and Saigo, "Packaging of tRNA and 6 S Stable RNA into Bacteriophage MS2 Particles Produced in *Escherichia coli* Treated with 5–Fluorouracil," *Virology*, 119:209–213, 1982.

Shiba and Suzuki, "Localization of a Protein in the RNA–A Protein Complex of RNA Phage MS2," *Biochimica et Biophysica Acta*, 654:249–255, 1981.

Stockley et al., "Molecular Mechanism of RNA Phage Morphogenesis," *Int. J. Biochem.*, 26(10/11)1249–1260, 1994.

Stockley et al., "Probing Sequence–Specific RNA Recognition by the Bacteriophage MS2 Coat Protein," *Nuc Acids Res*, 23(13):2512–2518, 1995.

Valegard et al., "Crystal Structure of an RNA Bacteriophage Coat Protein–Operator Complex," *Nature*, 371:623–626, Oct. 1994.

Valegard et al., "The Three–dimensional Structure of the Bacterial Virus MS2," *Nature*, 345:36–41, May 1990.

van Gemen, "A One–Tube Quantitative HIV–1 RNA NASBA Nucleic Acid Amplification Assay Using Electrochemiluminescent (ECL) Labelled Probes," *J Virological Methods*, 49:157–168, 1994.

Witherell et al., "Specific Interaction Between RNA Phage Coat Proteins and RNA," *Proc Nuc Acid Res Molec Biol*, 40:185–220, 1991.

Witherell et al., "Cooperative Binding of R17 Coat Protein to RNA," *Biochem*, 29:11051–11057, 1990.

Young et al., "Detection of Hepatitis C Virus RNA by a Combined Reverse Transcription–Polymerase Chain Reaction Essay," *J Clinical Microbiol*, 31(4):882–886, Apr. 1993.

SEQUENCE LISTING ( 1 ) GENERAL INFORMATION:

( i i i ) NUMBER OF SEQUENCES: 8

( 2 ) INFORMATION FOR SEQ ID NO:1:

( i ) SEQUENCE CHARACTERISTICS:
        ( A ) LENGTH: 23 base pairs
        ( B ) TYPE: nucleic acid ( C ) STRANDEDNESS: single
( D ) TOPOLOGY: linear ( x i ) SEQUENCE DESCRIPTION: SEQ ID NO:1:

```
CCTTTCGGGG TCCTGCTCAA CTT                                                    23
```

( 2 ) INFORMATION FOR SEQ ID NO:2:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:2:

```
GATTAGATCT GAGTTGAACT TCTTTGTTGT CTTC                                        34
```

( 2 ) INFORMATION FOR SEQ ID NO:3:

( i ) SEQUENCE CHARACTERISTICS:
        ( A ) LENGTH: 1718 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:3:

```
CCATGGCTAT CGCTGTAGGT AGCCGGAATT CCATTCCTAG GAGGTTTGAC CTGTGCGAGC            60
TTTTAGTACC CTTGATAGGG AGAACGAGAC CTTCGTCCCC TCCGTTCGCG TTTACGCGGA           120
CGGTGAGACT GAAGATAACT CATTCTCTTT AAAATATCGT TCGAACTGGA CTCCCGGTCG           180
TTTTAACTCG ACTGGGGCCA AAACGAAACA GTGGCACTAC CCCTCTCCGT ATTCACGGGG           240
GGCGTTAAGT GTCACATCGA TAGATCAAGG TGCCTACAAG CGAAGTGGGT CATCGTGGGG           300
TCGCCCGTAC GAGGAGAAAG CCGGTTTCGG CTTCTCCTC GACGCACGCT CCTGCTACAG            360
CCTCTTCCCT GTAAGCCAAA ACTTGACTTA CATCGAAGTG CCGCAGAACG TTGCGAACCG           420
GGCGTCGACC GAAGTCCTGC AAAAGGTCAC CCAGGGTAAT TTTAACCTTG GTGTTGCTTT           480
AGCAGAGGCC AGGTCGACAG CCTCACAACT CGCGACGCAA ACCATTGCGC TCGTGAAGGC           540
GTACACTGCC GCTCGTCGCG GTAATTGGCG CCAGGCGCTC CGCTACCTTG CCCTAAACGA           600
AGATCGAAAG TTTCGATCAA AACACGTGGC CGGCAGGTGG TTGGAGTTGC AGTTCGGTTG           660
GTTACCACTA ATGAGTGATA TCCAGGGTGC ATATGAGATG CTTACGAAGG TTCACCTTCA           720
AGAGTTTCTT CCTATGAGAG CCGTACGTCA GGTCGGTACT AACATCAAGT TAGATGGCCG           780
TCTGTCGTAT CCAGCTGCAA ACTTCCAGAC AACGTGCAAC ATATCGCGAC GTATCGTGAT           840
ATGGTTTTAC ATAAACGATG CACGTTTGGC ATGGTTGTCG TCTCTAGGTA TCTTGAACCC           900
ACTAGGTATA GTGTGGGAAA AGGTGCCTTT CTCATTCGTT GTCGACTGGC TCCTACCTGT           960
AGGTAACATG CTCGAGGGCC TTACGGCCCC CGTGGGATGC TCCTACATGT CAGGAACAGT          1020
TACTGACGTA ATAACGGGTG AGTCCATCAT AAGCGTTGAC GCTCCCTACG GTGGACTGT           1080
GGAGAGACAG GGCACTGCTA AGCCCAAAT CTCAGCCATG CATCGAGGGG TACAATCCGT           1140
ATGGCCAACA ACTGGCGCGT ACGTAAAGTC TCCTTTCTCG ATGGTCCATA CCTTAGATGC          1200
GTTAGCATTA ATCAGGCAAC GGCTCTCTAG ATAGAGCCCT CAACCGGAGT TTGAAGCATG          1260
GCTTCTAACT TTACTCAGTT CGTTCTCGTC GACAATGGCG GAACTGGCGA CGTGACTGTC          1320
GCCCCAAGCA ACTTCGCTAA CGGGGTCGCT GAATGGATCA GCTCTAACTC GCGTTCACAG          1380
GCTTACAAAG TAACCTGTAG CGTTCGTCAG AGCTCTGCGC AGAATCGCAA ATACACCATC          1440
AAAGTCGAGG TGCCTAAAGT GGCAACCCAG ACTGTTGGTG GTGTAGAGCT TCCTGTAGCC          1500
```

```
GCATGGCGTT CGTACTTAAA TATGGAACTA ACCATTCCAA TTTTCGCTAC GAATTCCGAC    1560

TGCGAGCTTA TTGTTAAGGC AATGCAAGGT CTCCTAAAAG ATGGAAACCC GATTCCCTCA    1620

GCAATCGCAG CAAACTCCGG CATCTACTAA TAGACGCCGG CCATTCAAAC ATGAGGATTA    1680

CCCATGTCGA AGACAACAAA GAAGTTCAAC TCAGATCT                            1718
```

( 2 ) INFORMATION FOR SEQ ID NO:4:

( i ) SEQUENCE CHARACTERISTICS:
        ( A ) LENGTH: 37 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:4:

```
GATTGGTACC TGCTATGTCA GTTCCCCTTG GTTCTCT                                37
```

( 2 ) INFORMATION FOR SEQ ID NO:5:

( i ) SEQUENCE CHARACTERISTICS:
        ( A ) LENGTH: 41 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:5:

```
GATTAGATCT AAGTTGGAGG ACATCAAGCA GCCATGCAAA T                           41
```

( 2 ) INFORMATION FOR SEQ ID NO:6:

( i ) SEQUENCE CHARACTERISTICS:
        ( A ) LENGTH: 1867 base pairs
        ( B ) TYPE: nucleic acid
        ( C ) STRANDEDNESS: single
        ( D ) TOPOLOGY: linear ( x i ) SEQUENCE DESCRIPTION: SEQ ID NO:6:

```
CCATGGCTAT CGCTGTAGGT AGCCGGAATT CCATTCCTAG GAGGTTTGAC CTGTGCGAGC      60

TTTTAGTACC CTTGATAGGG AGAACGAGAC CTTCGTCCCC TCCGTTCGCG TTTACGCGGA     120

CGGTGAGACT GAAGATAACT CATTCTCTTT AAAATATCGT TCGAACTGGA CTCCCGGTCG     180

TTTTAACTCG ACTGGGGCCA AAACGAAACA GTGGCACTAC CCCTCTCCGT ATTCACGGGG     240

GGCGTTAAGT GTCACATCGA TAGATCAAGG TGCCTACAAG CGAAGTGGGT CATCGTGGGG     300

TCGCCCGTAC GAGGAGAAAG CCGGTTTCGG CTTCTCCCTC GACGCACGCT CCTGCTACAG     360

CCTCTTCCCT GTAAGCCAAA ACTTGACTTA CATCGAAGTG CCGCAGAACG TTGCGAACCG     420

GGCGTCGACC GAAGTCCTGC AAAAGGTCAC CCAGGGTAAT TTTAACCTTG GTGTTGCTTT     480

AGCAGAGGCC AGGTCGACAG CCTCACAACT CGCGACGCAA ACCATTGCGC TCGTGAAGGC     540

GTACACTGCC GCTCGTCGCG GTAATTGGCG CCAGGCGCTC CGCTACCTTG CCCTAAACGA     600

AGATCGAAAG TTCGATCAA ACACGTGGC CGGCAGGTGG TTGGAGTTGC AGTTCGGTTG      660

GTTACCACTA ATGAGTGATA TCCAGGGTGC ATATGAGATG CTTACGAAGG TTCACCTTCA     720

AGAGTTTCTT CCTATGAGAG CCGTACGTCA GGTCGGTACT AACATCAAGT TAGATGGCCG     780

TCTGTCGTAT CCAGCTGCAA ACTTCCAGAC AACGTGCAAC ATATCGCGAC GTATCGTGAT     840

ATGGTTTTAC ATAAACGATG CACGTTTGGC ATGGTTGTCG TCTCTAGGTA TCTTGAACCC     900

ACTAGGTATA GTGTGGGAAA AGGTGCCTTT CTCATTCGTT GTCGACTGGC TCCTACCTGT     960

AGGTAACATG CTCGAGGGCC TTACGGCCCC CGTGGGATGC TCCTACATGT CAGGAACAGT    1020
```

| | | | | | | |
|---|---|---|---|---|---|---|
| TACTGACGTA | ATAACGGGTG | AGTCCATCAT | AAGCGTTGAC | GCTCCCTACG | GGTGGACTGT | 1080 |
| GGAGAGACAG | GGCACTGCTA | AGGCCCAAAT | CTCAGCCATG | CATCGAGGGG | TACAATCCGT | 1140 |
| ATGGCCAACA | ACTGGCGCGT | ACGTAAAGTC | TCCTTTCTCG | ATGGTCCATA | CCTTAGATGC | 1200 |
| GTTAGCATTA | ATCAGGCAAC | GGCTCTCTAG | ATAGAGCCCT | CAACCGGAGT | TTGAAGCATG | 1260 |
| GCTTCTAACT | TTACTCAGTT | CGTTCTCGTC | GACAATGGCG | GAACTGGCGA | CGTGACTGTC | 1320 |
| GCCCCAAGCA | ACTTCGCTAA | CGGGGTCGCT | GAATGGATCA | GCTCTAACTC | GCGTTCACAG | 1380 |
| GCTTACAAAG | TAACCTGTAG | CGTTCGTCAG | AGCTCTGCGC | AGAATCGCAA | ATACACCATC | 1440 |
| AAAGTCGAGG | TGCCTAAAGT | GGCAACCCAG | ACTGTTGGTG | GTGTAGAGCT | TCCTGTAGCC | 1500 |
| GCATGGCGTT | CGTACTTAAA | TATGGAACTA | ACCATTCCAA | TTTTCGCTAC | GAATTCCGAC | 1560 |
| TGCGAGCTTA | TTGTTAAGGC | AATGCAAGGT | CTCCTAAAAG | ATGGAAACCC | GATTCCCTCA | 1620 |
| GCAATCGCAG | CAAACTCCGG | CATCTACTAA | TAGACGCCGG | CCATTCAAAC | ATGAGGATTA | 1680 |
| CCCATGTCGA | AGACAACAAA | GAAGTTCAAC | TCAGATCTAA | GTTGGAGGAC | ATCAAGCAGC | 1740 |
| CATGCAAATG | TTAAAACATA | GCACTATAGA | ACTCTGCAAG | CCTCGAGTGA | GAGTGCATCC | 1800 |
| AGTGCATGCA | GGGCCTATTG | CACCAGGCCA | GATGAGAGAA | CCAAGGGGAA | CTGACATAGC | 1860 |
| AGGTACC | | | | | | 1867 |

( 2 ) INFORMATION FOR SEQ ID NO:7:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( x i ) SEQUENCE DESCRIPTION: SEQ ID NO:7:

GCAGAAAGCG TCTAGCCATG GCGT        24

( 2 ) INFORMATION FOR SEQ ID NO:8:

( i ) SEQUENCE CHARACTERISTICS:
( A ) LENGTH: 24 base pairs
( B ) TYPE: nucleic acid
( C ) STRANDEDNESS: single
( D ) TOPOLOGY: linear ( x i ) SEQUENCE DESCRIPTION: SEQ ID NO:8:

CTCGCAAGCA CCCTATCAGG CAGT        24

RIBONUCLEASE RESISTANT VIRAL RNA STANDARDS

BACKGROUND OF THE INVENTION

In the last few years, diagnostic assays and assays for specific mRNA species have been developed based on the detection of specific nucleic acid sequences. These assays depend on such technologies as "RT-PCR" (Mulder, 1994), isothermal amplification (NASBA) (Van Gemen, 1994), and branched chain DNA (Pachl, 1995). Many of these assays have been adapted to determine the absolute concentration of a specific RNA species. These absolute quantification assays require the use of an RNA standard of which the precise amount has been previously determined. These RNA standards are usually synthesized by in vitro transcription or are the infectious agents themselves. The RNA is purified and then quantified by several different methods, such as absorbance at OD260, phosphate analysis, hyperchromicity or isotopic tracer analysis (Collins, 1995).

Quantifying viral RNA sequences in plasma is an important tool for assessing the viral load in patients with, for example, Human Immunodeficiency Virus (HIV), Hepatitis C Virus (HCV), and other viral diseases. Vital load is a measure of the total quantity of viral particles within a given patient at one point in time. In chronic infections viral load is a function of a highly dynamic equilibrium of viral replication and immune-mediated host clearance. The benefits of determining vital load include the ability to: 1) assess the degree of viral replication at the time of diagnosis—an estimate having prognostic implications, 2) monitor the effect of antiviral medications early in the disease course, and 3) quickly assess the effects of changing antiviral medications.

Presently, the most sensitive method available for HIV quantification in plasma employs "PCR". There are 4 major steps involved in PCR analysis of HIV:1) Sample preparation, 2) Reverse transcription, 3) Amplification, and 4) Detection. Variability in any of these steps will affect the final result. An accurate quantitative assay requires that each step is strongly controlled for variation. In the more rigorous PCR™ assay formats, a naked RNA standard is added to the denaturant just prior to the isolation of the viral RNA from plasma (Mulder, 1994). A less precise method is to add the standard to the viral RNA after it has been purified (Piatak, 1993). It is important that the RNA standards are precisely calibrated and that they withstand the rigors of the assay procedures.

There is a need for ribonuclease resistant RNA standards. RNA is susceptible to environmental ribonucleases. Producing ribonuclease-free reagents is non-trivial. A danger in using naked RNA as a standard for quantification is its susceptibility to ribonuclease digestion. Compromised standards generate inaccurate values. This problem can be compounded in clinical laboratory settings where the personnel are not usually trained in RNA handling. These factors introduce doubt as to the validity of the data generated.

Naked RNA standards are very susceptible to ribonuclease digestion. Some RNA based assays have been formatted so that users access an RNA standard tube only once and then discard it to minimize the possibility of contaminating the RNA standard with ribonucleases. However, the standards are aliquoted into microfuge tubes which are not guaranteed to be ribonuclease-free introducing another potential source for contamination. As well, there is a short period of time during which the RNA is exposed to a pipet tip before it is placed in the denaturing solution. If the piper tip is contaminated with ribonuclease then the RNA standard will be degraded and the assay compromised. Another disadvantage of using naked RNA standards are that they must be stored frozen. In the branched DNA HIV assay formatted by Chiron Corp., the potential for RNA degradation is so risky that their assays include single stranded DNA instead of RNA for their standard (Pachl, 1995). The DNA is calibrated against RNA. The DNA standard is much less likely to be degraded. Thus, there is a need for RNA standards which are resistant to ribonucleases and in which there is no doubt about the integrity of the standard. These standards would also be more convenient if they did not need to be stored frozen so that they could be used immediately, no thawing required.

RNA bacteriophages have long been used as model systems to study the mechanisms of RNA replication and translation. The RNA genome within RNA bacteriophages is resistant to ribonuclease digestion due to the protein coat of the bacteriophage. Bacteriophage are simple to grow and purify, and the genomic RNA is easy to purify from the bacteriophages. These bacteriophages are classified into subgroups based on serotyping. Serologically, there are four subclasses of bacteriophage, while genetically, there are two major subclasses, A and B (Stockley, 1994; Witherell, 1991). Bacteriophage MS2/R17 (serological group I) have been studied extensively. Other well-studied RNA bacteriophages include GA (group II), Q-beta (group III), and SP (group IV). The RNA bacteriophages only infect the male strains of *Escherichia coli*, that is, those which harbor the F' plasmid and produce an F pilus for conjugation.

The MS2 bacteriophage is an icosahedral structure, 275 Å in diameter, and lacks a tail or any other obvious surface appendage (Stockley, 1994). The bacteriophage has large holes at both the 5- and 3-fold axes which might be the exit points of the RNA during bacterial infection. The MS2 bacteriophage consists of 180 units of the bacteriophage Coat Protein (~14 kDa) which encapsidate the bacteriophage genome (see reviews, Stockley, 1994; Witherell, 1991). The MS2 RNA genome is a single strand encoding the (+) sense of 3569 nucleotides. The genes are organized from the 5' end as follows: The Maturase or A protein, the bacteriophage Coat Protein, a 75 amino acid Lysis Protein, and a Replicase subunit. The Lysis gene overlaps the Coat Protein gene and the Replicase gene and is translated in the +1 reading frame of the Coat Protein. Each bacteriophage particle has a single copy of Maturase which is required for interacting with the F pilus and thus mediating bacterial infection.

Packaging of the RNA genome by Coat Protein is initiated by the binding of a dimer of Coat Protein to a specific stem-loop region (the Operator or pac site) of the RNA genome located 5' to the bacteriophage Replicase gene. This binding event appears to trigger the complete encapsidation process. The sequence of the Operator is not as critical as the stem-loop structure. The Operator consists of ~21 nucleotides and only two of these residues must be absolutely conserved for Coat Protein binding.

The viral Maturase protein interacts with the bacteriophage genomic RNA at a minimum of two sites in the genome (Shiba, 1981). It is evidently not required for packaging. However, its presence in the bacteriophage particle is required to preserve the integrity of the genomic RNA against ribonuclease digestion (Argetsinger, 1966; Heisenberg, 1966).

Attempts to produce a viable, infectious recombinant RNA (reRNA) bacteriophage have been unsuccessful. The bacteriophage are very efficient at deleting heterologous sequences and the fidelity of the Replicase is poor such that point mutations occur at the rate of ~1×10$^{-4}$.

Pickett and Peabody (1993) performed experiments in which a non-bacteriophage RNA was encapsidated by MS2 Coat Protein. Their apparent goal was to determine if the 21 nucleotide Operator (pac site) would confer MS2-specific packagability to non-bacteriophage RNA in vivo. *E. coli* was co-transformed with two plasmids: one encoding MS2 Coat Protein and the other encoding β-galactosidase (lacZ). The lacZ gene was modified such that it had the MS2 Operator sequence cloned upstream of it. The *E. coli* were induced such that the Operator-lacZ hybrid RNA was co-expressed with the MS2 Coat Protein. The Coat Protein dimer bound to the Operator, triggering the encapsidation of the lacZ RNA to form "virus-like particles". The virus-like particles were purified by a CsCl gradient. The buoyant density of these virus-like particles had a much greater density distribution than did the wild-type MS2 bacteriophage. The MS2 banded tightly at 1.45 g/cc whereas the virus-like particles ranged in density from 1.3 to 1.45 g/cc, suggesting substantial heterogeneity in the RNA content of the virus-like particles. In other words, the Pickett and Peabody virus-like particles were packaging different lengths of RNA and/or different species of RNAs.

The results of the Pickett and Peabody work were not as expected. The lacZ RNA purified from these virus-like particles was degraded to a major species of ~500 bases as opposed to the expected full length 3000 bases. This 500 base RNA was only detectable by the sensitive Northern blotting procedure. The authors did not know if the degradation occurred before or after encapsidation, but suggested that these vital-like particles may be sensitive to ribonuclease digestion. It was found that the majority of the RNA packaged was actually 2 species, 1800 bases and 200 bases in size. These two RNA fragments were easily detected after gel electrophoresis and methylene blue staining. The 500 base Operator-lacZ RNA fragment was not visible by methylene blue staining. It was only detected by Northern blotting using a lacZ probe. These authors concluded that the 0.2 and 1.8 kb RNAs were derived from *E. coli* pre-16S rRNA. The host *E. coli* RNA was packaged in preference to the Operator-lacZ RNA indicating that the specificity of the Pickett and Peabody bacteriophage packaging system was poor.

In other experiments, Pickett and Peabody modified the packaging of the Operator-lacZ RNA by changing the ratios of the Coat Protein and Operator-lacZ RNA produced in *E. coli*. By increasing the concentration of the Operator-lacZ RNA and decreasing the concentration of the Coat Protein, they were able to encapsidate mainly the Operator-lacZ RNA and no detectable pre- 16S rRNA. These results suggested that the original Pickett and Peabody packaging strategy suffered in specificity because they were unable to reach and maintain the appropriate molar ratio of Coat Protein to Operator-lacZ RNA optimal for packaging the target RNA. Even in the second set of packaging experiments, the concentrations of the Coat Protein and Operator-lacZ RNA were only coarsely adjusted. The Pickett and Peabody system had no feedback mechanism to maintain the optimal ratio of Coat Protein to Operator-lacZ RNA for packaging.

In their second set of packaging experiments, Pickett and Peabody did not characterize the RNA that was packaged with the modified procedure. The RNA was not purified from the virus-like particles and assessed by, for example, gel electrophoresis. Furthermore, the virus-like particles in this experiment or the previous experiment were not characterized for their ability to protect the encapsidated lacZ RNA from ribonucleases. There was no discussion as to the yield of virus-like particles or Operator-lacZ RNA obtained from the Pickett and Peabody experiments.

In view of the above, there is a need for a ribonuclease-resistant RNA standard. However, up to this time, no standard meeting the requirements of such a standard has been available.

SUMMARY OF THE INVENTION

The present invention relates to a nucleic acid standard encapsidated in viral protein. In a preferred embodiment, the invention relates to a ribonuclease resistant recombinant RNA ("reRNA") standard. These "ARMORED RNA" (AR) standards are ribonuclease resistant due to the encapsidation of the reRNA by bacteriophage proteins. The intact RNA is easily extracted from the "ARMORED RNA" particles by common RNA extraction methods such as the guanidinium and phenol method (Chomczynski, 1987). The RNA in "ARMORED RNA" contains non-bacteriophage RNA sequence which is used in quantifying assays. These standards may be used for a variety of purposes such as quantitative RNA standards (to determine the absolute copy number of a specific RNA sequence), specifically to quantify the number of RNA viruses such as HIV and HCV in plasma or serum. They may also be used to quantify the expression of specific mRNA in cells or tissue by an "RT-PCR" assay. The standards may be used as qualitative RNA standards acting as positive controls in diagnostics which are RNA based or in "RT-PCR" assays to indicate that all of the reagents are functioning properly. These standards may be used to measure the integrity of an RNA isolation procedure by measuring the amount of degradation observed in the "ARMORED RNA" after it has been subjected to the isolation procedure by Northern blotting. They may be used as environmental tracers to follow the flow of groundwater or to label the waste of individual companies with a unique nucleic acid sequence which can be traced back to the offending company.

The present invention is particularly used for viral quantification. There are many new nucleic acid based assays in the process of being developed and/or marketed (Roche Diagnostic Systems, "AMPLICOR" HIV Monitor and "AMPLICOR" HCV Monitor tests; Organon Teknika, NASBA HIV kit; GenProbe, Transcription Mediated Amplification HIV kit); and Chiron Corp., branched DNA (bDNA) signal amplification assay for HIV and HCV. These assays detect pathogenic human viruses such as HIV and HCV in human plasma or serum. These assays are highly sensitive, detecting as little as 300 virions per ml of plasma. In their current format, several of these nucleic acid based assays use naked RNA for their quantitative standards. Unfortunately, these naked RNA standards are very susceptible to ribonuclease degradation and thus the results of the assay may be compromised.

In order to understand some aspects of the invention, it is necessary to understand the components of a bacteriophage, for example, the MS2 bacteriophage. The RNA genome is ~3.6 kb and encodes 4 different proteins: the Maturase, the Coat Protein, the Lysis Protein and the Replicase. The Coat Protein composes most of the mass of the MS2 bacteriophage particle. It is a small protein of ~14 kD in size but there are 180 molecules of this protein which encapsidate each molecule of the bacteriophage RNA genome. In total, the Coat Protein molecules provide ~2,500 kD of the total bacteriophage mass of ~3,500 kD. There is one molecule of Maturase protein per bacteriophage particle which is ~44 kD in size. The Maturase serves to protect the RNA genome from ribonuclease degradation and it is the receptor for the F pilus for *E. coli* infection. The Lysis Protein and the Replicase are not a component of the bacteriophage molecule. The Lysis Protein is involved in lysing the *E. coli* cell to release the bacteriophage particles. The Replicase protein and 3 other *E. coli* host proteins compose a protein complex which is responsible for replicating the RNA genome and synthesizing a large number of copies for packaging.

In this application, cis refers to a protein binding to the same RNA transcript species from which it was translated. Trans refers to a protein binding to an RNA transcript species other than the RNA transcript species from which it was translated.

The present invention contemplates a ribonuclease resistant recombinant RNA which is highly suitable as an RNA standard for quantifying RNA viruses, although it can be used as an RNA standard for RNA isolated from any source, such as cells from tissue culture. In particular, the structure of an RNA bacteriophage is modified to package a recombinant RNA (reRNA) molecule such that the reRNA consists of sequence encoding the Coat Protein and the Maturase of the bacteriophage and a non-bacteriophage RNA sequence. The non-bacteriophage RNA sequence within the reRNA sequence serves as an RNA standard for the quantification of a particular RNA sequence/target. Due to the packaging of the reRNA by bacteriophage proteins, the reRNA is highly resistant to degradation by ribonucleases. The non-bacteriophage RNA sequence may be of different lengths and sequences.

The "ARMORED RNA" can be calibrated to serve as RNA standards in quantitative assays to determine the absolute number of RNA viruses within a plasma sample. The "ARMORED RNA" can be subjected to extreme ribonuclease treatment without any degradation of the RNA standard. "ARMORED RNA" is very durable and can be stored for an indefinite time at 4° C., or even room temperature, in the presence of ribonucleases. There is no known RNA standard with these qualities. "ARMORED RNA" differs in several features from prior art virus-like particles such as those of Pickett and Peabody. The bacteriophage sequence of the reRNA of the Pickett and Peabody particles consisted only of the Operator sequence (or pac site) which is required for Coat Protein recognition of the RNA to initiate packaging. The "ARMORED RNA" contains 1.7 kb of bacteriophage RNA sequence encoding the Maturase, the Coat Protein and the pac site. The inclusion of the long stretch of bacteriophage sequence within the packaged reRNA may contribute substantially to forming a macromolecular structure most similar to the wild-type MS2 structure. Further, there may be other, as of yet uncharacterized, sequences within the bacteriophage RNA that recognizes Coat Protein and Maturase that contribute to assembling the bacteriophage particle into a structure that protects the packaged RNA. Non-bacteriophage RNAs can be packaged by Coat Protein alone as demonstrated by Pickett and Peabody but these non-bacteriophage RNA sequences apparently do not produce a ribonuclease resistant structure. Besides maximizing the possibility of assuming the correct bacteriophage structure, the inclusion of the extra bacteriophage sequence in the "ARMORED RNA", as opposed to the Pickett and Peabody virus like particles, also increases the specificity of the RNA to be packaged by the bacteriophage proteins. The Pickett and Peabody virus like particles contained mainly the host *E. coli* pre-rRNA over the target RNA unless the ratio of the Coat Protein to reRNA was decreased.

A preferred strategy for synthesizing the "ARMORED RNA" is one that has been optimized by producing a self-regulating feedback mechanism to maintain the optimal ratio of Coat Protein to reRNA for assembly. The Coat Protein is encoded in the reRNA and it is only available for translation in its unassembled form. Thus, when the appropriate concentration of Coat Protein has been translated from the reRNA, it begins to package the reRNA. More Coat Protein cannot be translated until more reRNA is transcribed from the recombinant plasmid. The Pickett and Peabody strategy lacked a mechanism for maintaining a constant ratio between these two molecules. Pickett and Peabody used a trans mechanism for packaging the Operator-lacZ RNA. The Coat Protein RNA was transcribed from a different plasmid and therefore, the Coat Protein was being translated from a different RNA than it was to package. Since there was no Operator on the Coat Protein RNA, the Coat Protein RNA is continually being transcribed and the Coat Protein is continually being translated. After induction, there is no regulation of the synthesis of the Coat Protein. Similarly, there is no control of the transcription of the Operator-lacZ RNA. Thus the transcription of both RNAs is constitutive and translation of the Coat Protein is constitutive. In contrast, in some embodiments, the "ARMORED RNA" method is a cis method where the Coat Protein is being translated from the same RNA that is to be packaged. The production of the Coat Protein is regulated at the level of translation because once the concentration of Coat Protein is high enough, it encapsidates the RNA from which it is being translated and thus prevents any further Coat Protein from being translated from that RNA. By this autoregulatory method, the levels of Coat Protein cannot become so high that RNA is encapsidated in a non-specific fashion.

"ARMORED RNA" can be produced using minimal bacteriophage sequence that encodes the binding sites for Maturase and Coat Protein (or even less) while providing the Maturase and Coat Protein in trans. The maximal size of RNA that can be encapsidated and remain ribonuclease resistant remains to be defined. However, the wild type MS2 bacteriophage contains an RNA genome of ~3.6 kb. Since the structure of these bacteriophage is iscosahedral, it is likely that the maximal size will be ~4 kb. Thus, the potential to replace the sequences encoding the Maturase and the Coat Protein with a foreign sequence relevant to the user, may be advantageous. It should be obvious to one skilled in the art that a systematic set of experiments can be readily performed to determine the minimal amount of bacteriophage sequence necessary to produce "ARMORED RNA". One advantage of "ARMORED RNA" in these applications is that they are non-replicative and therefore, aberrantly high signals would not be detected due to viral replication.

The stability of "ARMORED RNA" indicates that the packaged RNA may withstand extreme environmental conditions. This property may be useful in using "ARMORED RNA" as molecular markers to trace the origins of pollutants. For instance, the "ARMORED RNA" could be spiked into the waste containers of different companies. The "ARMORED RNA" for each company would contain a unique nucleotide sequence which would identify that company. In the event of a spill, a sample would be taken, RNA would be isolated and "RT-PCR" performed to determine the unique sequence of the "ARMORED RNA" and identify the company responsible for the spill. In a related application, the "ARMORED RNA" could be used by environmentalists to trace the flow of groundwaters.

The aspects of the invention may be summarized as follows. In its most basic form, the invention contemplates a nucleic acid standard comprising recombinant nucleic acid segment encapsidated in viral Coat Protein. A preferred embodiment of the invention contemplates an RNA standard comprising a recombinant RNA segment. Encapsidation of the recombinant RNA segment in a viral Coat Protein can render it resistant to ribonuclease, hence the term "ARMORED RNA".

The viral Coat Protein may be any native or modified viral Coat Protein, but, in many preferred embodiments, the viral Coat Protein is a bacteriophage viral Coat Protein. Such bacteriophage viral Coat Proteins may be of an *E. coli* bacteriophage of genetic subclass A or B; in some preferred embodiments, the bacteriophage viral Coat Protein is of an *E. coli* bacteriophage of genetic subclass A. A bacteriophage viral Coat Protein can be of an *E. coli* bacteriophage in serological group I, II, II, or IV, with some preferred embodiments employing a bacteriophage viral Coat Protein from *E. coli* bacteriophage of serological group I. In certain specifically preferred embodiments, the bacteriophage viral Coat Protein is of an MS2/R17 bacteriophage. The bacteriophage viral Coat Protein may also be of a *Pseudomonas aeruginosa* RNA bacteriophage, for example, the *Pseudomonas aeruginosa* PRR1 or PP7 bacteriophage. The bacteriophage viral Coat Protein may further be of a filamentous bacteriophage, and, because such bacteriophage can comprise a longer RNA segment than many other bacteriophage, this is an embodiment of particular interest. Of course, the viral Coat Protein need not be from a bacteriophage, and the invention contemplates viral Coat Proteins from plant or animal virus, for example, tobacco mosaic virus, a feline immunodeficiency virus, and Rous sarcoma virus will all be useful. The viral Coat Protein may be a native or a modified viral Coat Protein. Modified viral Coat Proteins may be used to obtain certain desirable characteristics, such as greater or lesser viral Coat Protein binding to the RNA. Modified viral Coat Proteins may be made by any of a number of methods known to those of skill in the art, including PCR-based and other forms of site-directed mutagenesis.

In certain preferred embodiments, the RNA standard comprises a vital Maturase protein bound to a viral Maturase binding site on the recombinant RNA segment. The viral Maturase protein and/or viral Maturase protein binding site may be native or modified. Modifications in the base sequence of the Maturase binding site and in the amino acid sequence of the Maturase may be made by any of a number of methods know to those of skill. A viral Maturase binding site is found in the RNA sequence that encodes a native Maturase. Therefore, the recombinant RNA sequence may contain within itself an RNA coding for the Maturase. Further, since Maturase binding is purported to have some effect on the stability of RNA segments, it is contemplated that multiple Maturase binding sites and/or Maturase coding sequences may be included in the recombinant RNA segment.

The recombinant RNA segment may comprises a sequence coding a Replicase protein, and the Replicase protein may or may not be expressed or expressible from that sequence. In certain preferred embodiments, the sequence coding the Replicase protein codes a modified Replicase protein that is not active.

The recombinant RNA segment will typically comprises an Operator coding sequence, and, in many preferred embodiments, a viral Maturase protein binding site which may be included in a viral Maturase protein coding sequence. The recombinant RNA segment may further comprise a viral Coat Protein coding sequence of the type discussed above.

There are many embodiments of the recombinant RNA segment, a few examples of which are given below. In some very basic embodiments, the recombinant RNA segment comprises an Operator sequence and a viral Coat Protein sequence. In other embodiments, the recombinant RNA segment comprises at least two Operator sequences and a non-bacteriophage sequence. The recombinant RNA segment may comprise an Operator sequence, a sequence coding a viral Maturase protein, and a non-bacteriophage sequence. Further, in some preferred embodiments, the recombinant RNA segment comprises an Operator sequence, a sequence coding a vital Maturase protein, a sequence coding a viral Coat Protein and a non-bacteriophage sequence. The recombinant RNA segment may comprise an Operator sequence, at least two viral Maturase binding sites, a sequence coding a viral Maturase protein, a sequence coding a viral Coat Protein and a non-bacteriophage sequence. Alternatively, the recombinant RNA segment may comprise an Operator sequence, at least two vital Maturase binding sites, a sequence coding a viral Maturase protein, a sequence coding a viral Coat Protein, a non-bacteriophage sequence, and a sequence coding a Replicase protein. The recombinant RNA comprise all or part of the recombinant RNA segment is coded for in the sequence of pAR-1 or pAR-2.

In some preferred embodiments, the recombinant RNA segment comprises a bacteriophage sequence from an RNA bacteriophage and a non-bacteriophage sequence. The non-bacteriophage sequence may be inserted into a multiple cloning site. The non-bacteriophage sequence may be a viral, bacterial, fungal, animal, plant, or other sequence, although, in certain preferred embodiments it is a viral sequence. Multiple Operators may be on either terminus of the non-bacteriophage sequence, or may flank the sequence.

The non-bacteriophage sequence is often a sequence adapted for use as a standard in detection and/or quantification of an RNA by, for example, PCR-based procedures. In specific embodiments, the non-bacteriophage sequence is a sequence adapted for use in detection and/or quantification of an RNA of diagnostic value. For example, the non-bacteriophage sequence can be a sequence, adapted for use as a standard in detection and/or quantification of HIV-1, HIV-2, HCV, HTLV-1, HTLV-2, hepatitis G, an enterovirus, or a blood-borne pathogen. In some particularly interesting embodiments, the non-bacteriophage sequence is adapted for use in the detection of such viral diseases as HIV-1, HIV-2, HCV, HTLV-1, or HTLV-2. Adaptation of the non-bacteriophage sequence can be accomplished in any manner that will render the sequence suitable for detection and or quantification of the tested RNA. In some embodiments, the non-bacteriophage sequence adapted for use as a standard in detection and/or quantification of an RNA of interest by modifying the native RNA sequence to be detected or monitored so that it is distinguishable from the native sequence. For example, detection an/or quantification of HIV-1 can be accomplished with a non-bacteteriophage sequence comprising a modified HIV-1 sequence. The RNA standard may comprise a non-bacteriophage sequence adapted for use as a standard in detection and/or quantification of a blood-borne pathogen, such as a plasmodium, trypanosome, *Francisella tularensis*, or *Wucheria bancrofti*.

The bacteriophage sequence of the recombinant RNA segment may be a sequence from any *E. coli* bacteriophage of any genetic subclass, for example, subclass A. Further the bacteriophage sequence may be a sequence from an *E. coli* bacteriophage in serological group I, II, III, or IV. In certain embodiments, the bacteriophage sequence is a sequence from an MS2/R17 bacteriophage. Of course, the bacteriophage sequence can also be a sequence from a *Pseudomonas aeruginosa* RNA bacteriophage, such as the PRR1 or PP7 bacteriophage, or a filamentous bacteriophage.

Other embodiments of the invention contemplate recombinant RNA segment comprising various of the sequences discussed above. The recombinant RNA segment may be encapsidated in viral Coat Protein, or free from viral Coat Protein. For example, the recombinant RNA may be free of viral Coat Protein during the RNA standard production process or during an assay after isolation of the recombinant RNA segment from the viral Coat Protein. The recombinant RNA may be of any of the various forms discussed above, and may comprise Operator site(s), Maturase binding site(s), Coat Protein coding sequence(s), Maturase coding sequence (s), non-bacteriophage sequence(s), multiple cloning site(s), Replicase coding sequence(s), active or non-active Lysis Protein coding sequence(s) and/or other sequences.

The invention also contemplates DNA vectors adapted for use in the synthesis of a RNA standard comprising recombinant RNA segment encapsidated in viral Coat Protein. Such vectors are transfected into cells, for example *E. coli*, and function to cause the cells to produce RNA encapsidated in viral Coat Protein. A basic vector may comprise a sequence coding an Operator sequence and a viral Coat Protein sequence. Alternatively, the vector may comprise a sequence coding two Operator sequences and a non-bacteriophage sequence. In some embodiments, the vector will comprise a sequence encoding an Operator sequence, a sequence coding a viral Maturase binding site, and a multiple cloning site. The multiple cloning site may be either downstream or upstream of a sequence encoding a viral Maturase binding site. The vector of may further comprise a sequence coding a viral Maturase protein and/or a Maturase binding site. The sequence coding the viral Maturase binding site may be comprised within the sequence coding the viral Maturase protein. Certain preferred embodiments comprise a sequence coding a viral Coat Protein gene, an Operator sequence, and a multiple cloning site. A DNA sequence coding a non-bacteriophage sequence may be inserted into the multiple cloning site of such a DNA vector, and the non-bacteriophage sequence may be any of the sequences discussed above.

The invention contemplates collection tubes containing a recombinant nucleic acid standard comprising recombinant nucleic acid encapsidated in viral Coat Protein. Such collection tubes may be adapted for use in collection of a body fluid such as blood, urine, or cerebrospinal fluid. For example, the collection tube may be a vacuum tube for the drawing of blood. Such collection tubes can streamline a diagnostic procedure by providing a nucleic acid standard in a body fluid sample at the time of drawing of the fluid and eliminating the need to add the standard as a part of the assay procedure.

The present invention contemplates methods for assaying for the presence of a tested nucleic acid using the nucleic acid standards described above. Such methods generally comprise the steps of: (1) obtaining a sample to be assayed; (2) obtaining a nucleic acid standard comprising, encapsidated in viral Coat Protein, a recombinant nucleic acid segment comprising a sequence coding a standard nucleic acid; (3) isolating nucleic acid from the sample; (4) isolating the recombinant nucleic acid segment from the viral Coat Protein; (5) admixing the nucleic acid from the sample and the recombinant nucleic acid segment; (6) and assaying for the presence of the tested nucleic acid. In preferred embodiments, the admixing of the nucleic acid from the sample and the recombinant nucleic acid segment comprises admixing the sample and the nucleic acid standard prior to isolation so that isolation of nucleic acid from the sample and the recombinant nucleic acid sequence is performed in the same procedure. This streamlines the procedure and assures that any tested nucleic acid and the recombinant nucleic acid of the nucleic acid standard are processed in parallel in the same reaction. Such parallel processing eliminates many variables that could compromise the results of the assay.

The assay may be any for that would employ a nucleic acid standard, although many preferred embodiments comprise PCR analysis. One of the advantages of the nucleic acid standards of the invention is that they allow for quantitative assays, such as quantitative PCR. In PCR procedures, the recombinant nucleic acid segment is typically an RNA comprising a sequence coding a standard RNA. Typically quantitative assays will comprise comparing an amount of tested RNA PCR product with an amount of standard RNA PCR product. In PCR procedures, the tested nucleic acid is often an RNA. PCR analysis will usually comprise: (1) employing a reverse transcription procedure; (2) amplifying PCR product; and (3) detecting PCR product. In certain embodiments, the amplification step involves co-amplification of any tested RNA PCR product with standard RNA PCR product. Such co-amplification can be achieved via the use of a single primer set adapted for amplification of both tested RNA PCR product and standard RNA PCR product. The nucleic acid standard may be of any composition described either explicitly or implicitly above. The non-bacteriophage sequence is a sequence in such procedures adapted for use as a standard in detection and/or quantification of an RNA. In some preferred embodiments, the assay may be employed to detect and/or quantify viral loads in infection with HIV-1, HIV-2, HCV, HTLV-1, HTLV-2, hepatitis G, an enterovirus, or a blood-borne pathogen. Presently more preferred embodiments contemplate the detection and/or quantification of HIV-1, HIV-2, or HCV using an RNA standard comprises a recombinant RNA with a modified HIV-1, HIV-2, or HCV sequence.

One specific method of the invention contemplates assaying for the presence of an RNA of diagnostic value by a method comprising: (1) obtaining a sample to be assayed; (2) obtaining an RNA standard comprising, encapsidated in a bacteriophage Coat Protein, a recombinant RNA segment comprising a sequence coding a standard RNA; (3) admixing the sample with the RNA standard; (4) isolating RNA from the admixture; and assaying for the presence of the RNA of diagnostic value with a PCR analysis.

The invention contemplates methods of making a nucleic acid standard comprising a recombinant nucleic acid segment encapsidated in viral Coat Protein comprising: (1) obtaining a vector comprising a nucleic acid sequence coding a recombinant nucleic acid segment comprising a sequence coding an Operator sequence, and a non-bacteriophage sequence; (2) transfecting the vector into a cell; (3) providing a viral Coat Protein; and (4) culturing the cell under conditions allowing for transcription of the recombinant nucleic acid segment and encapsidation of the recombinant nucleic acid segment in viral Coat Protein. The recombinant nucleic acid segment may be RNA or DNA. The nucleic acid standard may be pified from the cells in which it is expressed by any of a number of manners known to those of skill for the separation of viral particles from cells. The cell may be any form of cell, although typically a bacterial cell, such as *E. coli* is employed.

Particularly preferred are methods of making RNA standards comprising a recombinant RNA segment encapsidated in vital Coat Protein, which methods comprise: (1) obtaining a vector comprising a DNA sequence coding a recombinant RNA segment comprising a sequence coding an Operator sequence and a non-bacteriophage sequence; (2) transfecting the vector into a cell; (3) providing a viral Coat Protein; and (4) culturing the cell under conditions allowing for transcription of the recombinant RNA segment and encapsidation of the recombinant RNA segment in viral Coat Protein. In many preferred embodiments, the recombinant RNA will comprise a Maturase binding sequence.

The provision of the viral Coat Protein can be by any number of means. For example, the protein can be expressed separately from the transcription of the recombinant RNA segment and added into the culture medium in a concentration such that the recombinant RNA becomes encapsidated once transcribed. However, in most preferred embodiments, the provision of the Coat Protein comprises: (1) obtaining a nucleic acid segment coding a viral Coat Protein; (2) transfecting the nucleic acid segment coding the viral Coat Protein into the cell; and (3) culturing the cell under conditions allowing for expression of the viral Coat Protein. In this embodiment, the nucleic acid segment coding the viral Coat Protein may be a DNA sequence comprised in the vector comprising the DNA sequence coding the recombinant RNA segment. The DNA sequence coding the vital Coat Protein may be located cis to the DNA sequence coding the recombinant RNA segment. Further, the DNA sequence coding the vital Coat Protein can be located in the DNA sequence coding the recombinant RNA segment. Alternatively, the DNA sequence coding the viral Coat Protein may be located trans to the DNA sequence coding the recombinant RNA segment, although this is not typical of preferred embodiments.

The method of making an RNA standard may comprise the further step of providing a viral Maturase protein. The provision of the viral Maturase protein can be by any number of means. For example, the protein can be expressed separately from the transcription of the recombinant RNA segment and added into the culture medium in a concentration such that the recombinant RNA becomes encapsidated once transcribed. However, in most preferred embodiments, the provision of the Maturase protein comprises: (1) obtaining a nucleic acid segment coding a vital Maturase protein; (2) transfecting the nucleic acid segment coding the viral Maturase protein into the cell; and (3) culturing the cell under conditions allowing for expression of the viral Maturase protein. In this case, the nucleic acid segment coding the vital Maturase protein may be a DNA sequence comprised in the vector comprising the DNA sequence coding the recombinant RNA segment. The DNA sequence coding the viral Maturase protein may be located cis to the DNA sequence coding the recombinant RNA segment. Further, the DNA sequence coding the viral Maturase protein can be located in the DNA sequence coding the recombinant RNA segment. Alternatively, the DNA sequence coding the vital Maturase protein may be located trans to the DNA sequence coding the recombinant RNA segment, although this is not typical of preferred embodiments. The recombinant RNA sequence, may, of course, be any of those discussed or suggested explicitly or implicitly above.

A preferred embodiment of the method of making an RNA standard comprising a recombinant RNA segment encapsidated in viral Coat Protein comprises: (1) obtaining a vector comprising a DNA sequence coding a recombinant RNA segment comprising a sequence coding an Operator sequence, a sequence coding a vital Maturase binding site, and a non-bacteriophage sequence; (2) transfecting the vector into a cell; (3) obtaining a DNA segment coding a vital Coat Protein and transfecting the nucleic acid segment coding the viral Coat Protein into the cell; (4) obtaining a DNA segment coding a viral Maturase protein and transfecting the nucleic acid segment coding the viral Maturase protein into the cell; and (5) culturing the cell under conditions allowing for transcription of the recombinant RNA segment, expression of the viral Coat Protein and the viral Maturase protein, and encapsidation of the recombinant RNA segment in viral Coat Protein. In preferred embodiments of this aspect of the invention, the DNA segment coding the viral Coat Protein is comprised in the vector comprising the DNA sequence coding the recombinant RNA segment. More preferably, the DNA sequence coding the viral coat protein is located cis to the DNA sequence coding the recombinant RNA segment. In preferred embodiments of this invention, the DNA segment coding the viral Maturase protein is comprised in the vector comprising the DNA sequence coding the recombinant RNA segment and, more preferably, located cis to the DNA sequence coding the recombinant RNA segment.

The invention also contemplates methods of making RNA in vivo comprising: (1) obtaining a vector comprising a DNA sequence coding a recombinant RNA segment comprising a sequence coding an Operator sequence, a sequence coding a viral Maturase binding site, and a non-bacteriophage sequence; (2) transfecting the vector into a cell; (3) obtaining a DNA segment coding a vital Coat Protein and transfecting the nucleic acid segment coding the viral Coat Protein into the cell; (4) obtaining a DNA segment coding a vital Maturase protein and transfecting the nucleic acid segment coding the viral Maturase protein into the cell; and (5) culturing the cell under conditions allowing for transcription of the recombinant RNA segment, expression of the viral Coat Protein and the viral Maturase protein, and encapsidation of the recombinant RNA segment in viral Coat Protein. These methods may further comprise the step of isolating the recombinant RNA segment from the Coat Protein, and this allows for the production of a large mount of desired RNA in vivo, i.e., within bacterial cells. The isolated RNA segment may then be treated to obtain an RNA segment comprising the non-bacteriophage sequence. For example molecular biology tools may be used to excise undesired RNA from the non-bacteriophage sequence, or a portion thereof. The desired RNA segment may then be purified by means known in the art. The DNA vectors, RNA segments, cells, etc. employed and obtained in this method of in vivo transcription may be any of those described above.

Following long-standing patent law convention, the words "a" and "an", when used in the specification including the claims, denote one or more.

BRIEF DESCRIPTION OF THE DRAWINGS

The following drawings form part of the specification and are included to further demonstrate certain aspects of the present invention. The invention may be better understood by reference to one or more of these drawings in combination with the detailed description of specific embodiment presented herein.

DESCRIPTION OF ILLUSTRATIVE EMBODIMENTS

Figure 1:
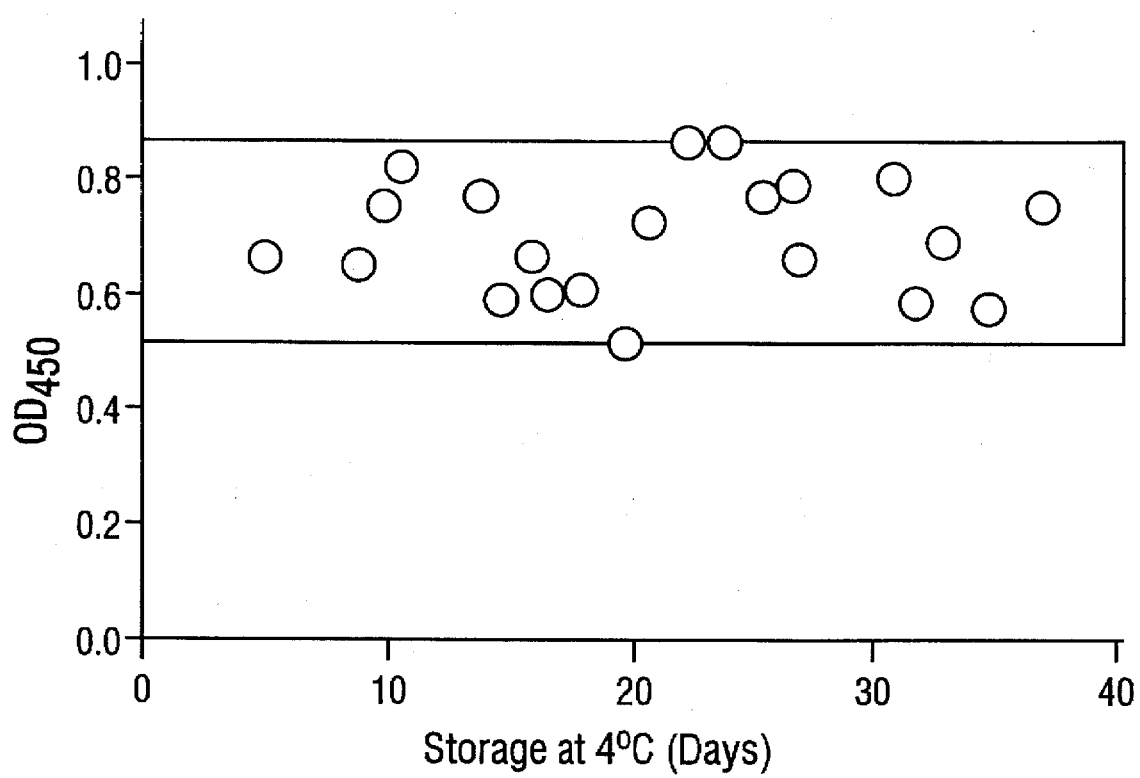
FIG. 1. Consistency of the signal produced by the AR-2 standard which was stored at 4° C. AR-2 standard (80 QS RNA equivalents) was added to 0.2 ml of HIV positive serum and processed using the "AMPLICOR" HIV Monitor test. Twenty one assays were performed over a 38 day period using the same stock of AR-2 standard stored at 4° C. in water.

The following examples describe the production of Armored RNA™ standards, illustrate the degree to which the reRNA are protected from ribonuclease activity, and applications of the invention.

EXAMPLE I

Construction of Armored RNA™ And Use of Armored RNA to Quantify HIV

1. Construction of Armored RNA™

The "ARMORED RNA" standard is a modified version of the RNA bacteriophage MS2 which contains only the Maturase and Coat Protein genes. A full-length cDNA clone of the RNA bacteriophage MS2 (pMS27) contains all the genes necessary to produce wild-type, infectious MS2 bacteriophage (Shaklee, 1990).

A fragment of DNA was synthesized from pMS27 by "PCR" encoding the Maturase and the Coat Protein of MS2 using the primers 5'CCTTTCGGGG TCCTGCTCAA CTT 3' (sense primer SEQ ID NO:1) and 5' GATTAGATCT GAGTTGAACT TCTTTGTTGT CTTC 3' (antisense primer SEQ ID NO:2). A BglII restriction sequence was incorporated into the antisense primer to mediate the cloning of this PCR™ product into the expression vector pSE380 (In Vitrogen Corporation). The PCR™ product was purified using the "GENIEPREP" (Ambion, Inc; "GENIEPREP" is a DNA isolation kit that purifies plasmid DNA based on the alkaline lysis procedure (Birnboim, 1983)) and eluted from the glass fiber pad with 70 µl of water. The "PCR" fragment was digested with NcoI and BglII. Ten µl of 10x React 3 Buffer (0.5M Tris [pH 8.0]; 0.1M MgCl₂; 1M NaCl) 20 µl water and 3 µl of NcoI and BglII were added to the purified "PCR" product and incubated 37° C., 2.5h. An NcoI site is a naturally occurring sequence within the MS2 genome located just 5' of the start codon for the Maturase gene. The digested PCR™ product was again purified with "Genieprep" (Ambion, Inc.) and eluted with 70 µl of water.

The digested "PCR" fragment was ligated into the NcoI and BglII sites of vector pSE380. pSE380 previously digested with BglII and NcoI was combined with the BglII and NcoI digested "PCR" product in a 1x Ligation Buffer (50 mM Tris [pH 7.8]; 10 mM MgCl₂. 10 mM DTT; 1 mM ATP; 0.025 mg/ml acetylated BSA; Ambion, Inc.) with T4 DNA Ligase (Ambion, Inc.). The ligation reaction was incubated at room temperature (~21° C.), 4 h. Ligated product was transformed into competent E. coli strain DHSα cells and then spread onto $Cb_{100}$-LB plates, 37° C., 16 h. Some of the resulting colonies were picked, grown in $Cb_{25}$-LB medium, the plasmid DNA isolated using "GENIEPREP" (Ambion, Inc.) and then screened for a DNA insert with the same size as the "PCR" product by digesting the DNA with NcoI and BglII. The pSE380 vector contains the E. coli RNA Polymerase terminator sequence rrnBT₁T₂, 3' of the multiple cloning site, positions 709 to 866.

The resulting construct is named pAR-1 (SEQ ID NO:3). Both bacteriophage genes are downstream of the strong trc promoter which is regulated by the lacI protein expressed by pSE380. The Operator sequence (pac site) is present in the NcoI/BglII fragment just downstream of the Coat Protein sequence. A truncated version of the Lysis gene is also present but the peptide encoded is not an active form of the protein. pSE380 encodes lac $I^q$, the superrepressor, which is inactivated in the presence of IPTG. Thus, transcription of the bacteriophage genes is down-regulated until IPTG is added to the culture medium and the trc promoter is activated. Transcription is terminated by the rrnBT₁ ₜ₂ terminator sequence.

The Maturase protein, the Coat Protein and the RNA which encoded these proteins were used for the production of the stable, bacteriophage-like "ARMORED RNA" particle. The Maturase protein is hypothesized to be an important component of "ARMORED RNA" that is hypothesized to stabilize the bacteriophage-like particle and endow additional protection for the RNA contained within the bacteriophage like particle. Therefore, many preferred embodiments of the invention will include the Maturase protein. There is a binding site for Maturase protein within the Maturase coding sequence (Shiba, 1981). The Maturase binding site was hypothesized necessary to be included in the reRNA as sequence which contributed to the packaging of the reRNA. The Coat Protein is an important component because it makes up the bulk of the bacteriophage particle. It was hypothesized unnecessary to include the Lysis gene or the Replicase gene because neither gene is involved in packaging. The Replicase is not needed because E. coli RNA Polymerase transcribes from plasmid DNA the RNA sense (+) strand encoding Maturase and Coat Protein once transcription is induced. However, as mentioned previously, it may not be necessary to have the genes for the Maturase and Coat Protein in cis with the RNA standard. They might be supplied in trans from another vector or even incorporated into the E. coli chromosome.

Armored RNA™ was produced using the pAR-1 recombinant plasmid. E. coli strain DHSα harboring this plasmid were grown overnight, 200 rpm, 37° C. in LB medium (10 g/liter tryptone, 5 g/liter yeast extract, 10 g/liter NaCl in water, pH 7.0–7.5) with 25 µg/ml carbenicillin ($Cb_{25}$). 0.2 ml of the overnight culture was used to inoculate 2 ml of fresh $Cb_{25}$-LB medium and incubated 1.5 h, 37° C., 200 rpm. Expression was induced by adding IPTG to 1 mM and incubating 3 h, 37° C., 200 rpm.

The cells were pelleted and then resuspended in 0.25 ml of 5 mM $MgSO_4$:0.1M NaCl:50 mM Tris (pH 8.0) (Sonication Buffer). The cells were sonicated (Branson Sonifier 450) with the small sonication probe 50% duty cycle, unit 5 power for 5 pulses of the probe. The sonicate was iced 1 min and then the sonication step was repeated. The sonicate was centrifuged to pellet the cell debris. 20 µl of supernatant was incubated with 100 units of E. coli RNase 1 and 2 units of bovine pancreatic DNase 1, 37° C., 40 min, to eliminate E. coli RNA and DNA. After nuclease treatment, 15 µl of supernatant was electrophoresed on an agarose gel in TBE buffer and stained with Ethidium Bromide to assay for "ARMORED RNA".

The "ARMORED RNA" had a mobility of a 900–1000 base pair double stranded DNA fragment as compared to two different DNA size standards (lambda DNA digested with HindIII and pUC19 plasmid DNA digested with Sau 3A) which were also run on the gel with the "ARMORED RNA". The mobility was very similar to the wild-type MS2 bacteriophage mobility. Treatment of "ARMORED RNA" with DNase or RNase did not affect their intensity of staining or their electrophoretic mobility. Ribonuclease 1 (100 units; Ambion, Inc.) and DNase 1 (2 units; Ambion, Inc.) were added separately or together to 20 µl of the "ARMORED RNA" supernatant. The supernatant was incubated at 37° C. with these enzymes, 40 minutes and then fractionated on an 0.8% agarose gel in TBE buffer. Although the high molecular weight E. coli genomic DNA and the E. coli RNA were digested by the appropriate enzymes, there was no change to the signal of the "ARMORED RNA" except that it became more intense and resolved because presence of the E. coli nucleic acids in the supernatant tended to smear the signal of the "ARMORED RNA". However, the nucleases did degrade the genomic DNA and the host RNA.

Cells which were uninduced synthesized some "ARMORED RNA" but much less than the induced cells. Two cultures of pAR-1 in E. coli were grown to mid-log phase $Cb_{25}$-LB. One culture was then induced with 1 mM IPTG and the other was not. Both cultures were grown for another 3 h, 37° C., 200 rpm and then cultures were assayed for "ARMORED RNA" production. As assayed by gel electrophoresis and Ethidium Bromide staining, more "ARMORED RNA" was synthesized in the induced cells than in the uninduced. Cells were also induced for 16 h and this protocol resulted in the production of more "ARMORED RNA" than the 3 h induction. The ribonuclease resistance of the "ARMORED RNA" containing the 1.7 kb truncated bacteriophage RNA indicates that the full length 3.6 kb of the MS2 bacteriophage RNA genome is not required from the production of "ARMORED RNA" particles.

2. Construction of an Armored RNA™ HIV standard pAR-1 served as the backbone for the creation of a quantitative HIV RNA standard compatible with the "AMPLICOR" HIV Monitor kit (Roche Diagnostic Systems). This study shows one example of how "ARMORED RNA" can be employed.

The QS RNA is the naked RNA standard in the "AMPLICOR" HIV Monitor test. The QS RNA encodes a conserved sequence of the gag gene from HIV but also contains a 26 bp substitution of randomized sequence. This random sequence is used to distinguish the wild type HIV amplicon from the QS amplicon since the HIV RNA and the QS RNA are co-amplified in the Monitor test.

RT-PCR™ was applied to the naked QS RNA to produce a DNA fragment encoding the QS sequence and contained BglII and KpnI restriction sites. The primers used were 5'GATTGGTACC TGCTATGTCA GTTCCCCTTG GTTCTCT 3'(SEQ ID NO:4) and 5'GATTAGATCT AAGT-TGGAGG ACATCAAGCA GCCATGCAAA T 3'(SEQ ID NO:5). These primers correspond to the SK431 and SK462 primers respectively used in the Monitor kit (Mulder, 1994) except that a KpnI sequence was added to the SK431 primer and a BglII sequence was incorporated into the SK462 primer. The QS PCR™ product was digested with BglII and KpnI and ligated into the BglII and KpnI sites in pAR-1 creating the recombinant plasmid, pAR-2. The QS sequence is immediately downstream of the Maturase and Coat Protein genes.

An NcoI/KpnI fragment containing the Maturase, the Coat Protein and the QS RNA sequence was cloned into the NcoI/KpnI restriction sites of the expression vector, pSE380 (In Vitrogen Corp.) to produce pAR-2. Each of the regions of the insert is indicated below the DNA sequence including: NcoI (1>6), BglII (1713>1718), KpnI (1861>1866), Maturase coding sequence (53>1231), Coat Protein coding sequence (1258>1647), Lysis Protein (1601>1711), the Capture Sequence within the QS sequence (1757>1782), the QS Amplicon region ( 1720>1861), SK462 primer (1720>1749), SK431 primer (1861>1835), Maturase Binding Site (311>337), and Operator sequence or pac site (1667>1687) (SEQ ID NO:6).

pAR-2 in E. coli was induced with 1 mM IPTG in Cb25-LB at mid-log phase for 3 h, 37° C., 200 rpm. The induced cells were pelleted and then sonicated in the Sonication Buffer used for the AR-1 particles. Then cell debris was pelleted by centrifugation. The sonicate supernatant was incubated with RNase 1 (5 units/µl) and DNase 1 (0.1 units/µl), 37° C., 30 minutes and then fractionated on an agarose gel and visualized by Ethidium Bromide staining. The AR-2 particles were detected as a fluorescent band migrating at about 900 base pairs as compared to the DNA markers run on the same gel.

The AR-2 sonication supernatant containing the AR-2 particles was incubated under the same conditions as above with RNase 1 and DNase 1 except that the incubation was for 16 h. Another sample of AR-2 was incubated 16 h, 37° C. but nucleases were not added. These samples were fractionated on an agarose gel and compared to the AR-2 preparation which was stored at 4° C. The AR-2 signal was strongest in the sample which was treated with the nucleases because the nucleases degraded the nucleic acids which were masking the AR-2 signal.

The AR-2 were also isolated from culture supernatant. pAR-2 transformed E. coli were induced with 1 mM IPTG, 16 h in 50 ml of $Cb_{50}$-LB medium. Inoculation and induction were simultaneous. 0.4 ml lysozyme (50 mg/ml) was added to the culture and incubated 37° C., 200 rpm, 1 h followed by the incubation of the cell culture with 0.4 ml of 1-bromo-3-chloro-propane 37° C., 200 rpm, 10 min. The cell debris was pelleted by centrifugation in an SS34 rotor, 4° C., 9000 rpm, 10 min. The culture supernatant was transferred to fresh tubes and 0.015 ml of 1-bromo-3-chloro-propane was added. The culture supernatant was stored at 4° C. 0.015 ml of the culture supernatant was fractionated on an agarose gel and detected by ethidium bromide staining and UV fluorescence. AR-2 were detected in the supernatant as well as genomic DNA from E. coli. However, unlike the AR-2 isolated from E. coli cytoplasm, this AR-2 preparation did not contain detectable E. coli RNA. A 0.5 ml prep of AR-2 from the spent growth medium was treated with 10 units of DNaseI, 37° C., 70 min. As assessed by gel electrophoresis, DNaseI completely degraded the host DNA but did not affect the AR-2.

0.02 ml of the AR-1 and AR-2 particles isolated from E. coli cytoplasm by sonication, were treated with 2 units DNaseI and 100 units RNaseI, 37° C., 2 h and then 21° C., 16 h to degrade all host E. coli RNA and DNA. The AR preps were subjected to single tube RT-PCR™ using primer pairs specific for the QS amplicon, SK431 and SK462 (Mulder, 1994), and specific for the MS2 bacteriophage sequence, MS2-1 and MS2-2. The "ARMORED RNA" preps were diluted 10, 100 and 1000 fold in PBS. RT-PCR™ was performed with 1 µl of each of the "ARMORED RNA" dilutions using SK431/SK462 and MS2-1/MS2-2 primer pairs. Prior to the reverse transcription step, the "ARMORED RNA" preps were incubated at 95° C., 5 min to disrupt the protective protein coat of the "ARMORED RNA". The RNA was cooled on ice in the presence of the primers and then incubated with 100 units MMLV-RT, 42° C., 1 h. 2.5 μl Taq polymerase was added, followed by PCR™. The PCR™ products were fractionated by gel electrophoresis. Only the AR-2 generated the expected PCR™ product of 142 bp with the SK primers whereas the AR-1 and AR-2 generated a 411 bp product using the MS2 primers. These results were consistent with the AR-2 particles containing the QS RNA target and an MS2 RNA target while the AR-1 only contain the MS2 sequence.

Of course, the above protocol can be modified to produce almost any RNA standard of "ARMORED RNA" may be produced by cloning the DNA sequence (encoding the RNA sequence of interest) into the recombinant plasmid, pAR- 1. This plasmid encodes the Maturase, the Coat Protein and the Operator Sequence and there are many convenient restriction enzyme sites immediately downstream (3') of the BglII restriction site of pAR-1. These restriction sites are the same restriction sites originally encoded in the multiple cloning site of pSE380, from nucleotides 396 to 622. Thus, DNA fragments may be synthesized chemically for cloning into pSE380. Alternatively, "PCR" or "RT-PCR" may be used to synthesize long DNA fragments (>100 bp) using primers which introduce restriction sites at both termini of the DNA fragment. The "PCR" DNA fragments may be digested for cloning into pAR-1.

An advantage of using the larger gene fragments is that "PCR" primers to different regions of these genes may be used with a single "ARMORED RNA" standard and it is not necessary to construct a different "ARMORED RNA" standard for each "PCR" primer pair that might be used. If large fragments of HIV RNA sequence (1 to 3kb) are packaged into "ARMORED RNA", then the user has the option of using a variety of primer pairs for performing "RT-PCR". This type of construct may more readily conform to the primer pairs that the researcher is currently using and he would not need to change primer pairs in order to use the "ARMORED RNA" standard. The user is not limited to just one set of primer pairs as when using, for example, the short 142 base pair region used in the "AMPLICOR" assay.

Of course, the HIV sequences may contain modifications from the wild-type sequence which will allow the standard sequence to be distinguished from the wild-type for the purpose of using the "ARMORED RNA" in competitive "PCR" as quantitative standards. Such modifications include insertions, deletions and restriction enzyme sequences.

It is not known what is the maximum limit of non-bacteriophage RNA can be packaged as an "ARMORED RNA". However, the full length genome of MS2 is ~3.6 kb and pAR-1 encodes only ~1.7 kb of the MS2 genome. Therefore, it is very likely that as a minimum, at least 2 kb of non-bacteriophage RNA sequence can be encapsidated as "ARMORED RNA" and possibly more if the Maturase and Coat Protein genes are supplied in trans.

3. AR-2 used as a quantitative RNA standard for HIV

In the "AMPLICOR HIV" Monitor test, the naked QS RNA standard is added to the Lysis buffer just prior to using the Lysis buffer for isolating the HIV RNA from plasma or serum. It is in this manner that the QS RNA is added to the plasma sample and that the HIV RNA and the QS RNA are co-purified. After isolation, the RNA is subjected to "RT-PCR" using the Tth DNA polymerase which functions as a reverse transcriptase and a heat stable DNA polymerase. After "RT-PCR", the "PCR" products are incubated in the wells of an ELISA plate which contain oligonucleotides (capture probes) immobilized to the well bottoms. One set of wells has an oligonucleotide sequence which is complementary to the wild-type sequence of HIV. The other capture probe recognizes the unique sequence in the QS amplicon. Thus, the HIV capture probe hybridizes to the HIV amplicon while the QS capture probe hybridizes to the QS amplicon which result from the "RT-PCR" co-amplification. After hybridization, the amount of amplicon hybridized is detected enzymatically and colorimetrically using horse radish peroxidase. In the standard assay format recommended by the manufacturers, about "60 to 80" copies of the QS RNA standard are added to each sample for analysis, depending on the kit lot number.

To test "ARMORED RNA" in the "AMPLICOR HIV" Monitor test, the naked QS RNA, and the concentrated AR-1 and the AR-2 were subjected to the "AMPLICOR HIV" Monitor test. The QS RNA, AR-1 and AR-2 were added to the Lysis buffer, the RNA was isolated and then subjected to the "RT-PCR" procedure. The PCR™ products were detected on assay plates. The QS RNA produced the expected signal, the AR-1 were negative whereas the AR-2 produced a signal so strong that it was off-scale. Once the concentrated AR-2 prep was diluted a 30 million fold, the signal became comparable to the QS RNA standard. The AR-2 prep was diluted by 30 million to produce a stock of "ARMORED RNA" which was the equivalent of 8,000 copies of QS RNA per milliliter. 10 μl of this AR-2 stock produced the same signal in the "AMPLICOR" HIV Monitor assay as the recommended amount of the naked QS RNA standard provided with the kit.

The AR-2 were diluted in water and stored at 4° C. over a period of several months. The diluted AR-2 were calibrated to produce a signal similar to the QS RNA in the "AMPLICOR" assay. Numerous "AMPLICOR" assays have been performed with the same diluted stock of AR-2. During a 38 day period, there has been no detectable decrease in the signal produced with the AR-2, highlighting the durability of these RNA standards (FIG. 1). This result is illustrative of the stability of the AR particles considering that this AR-2 stock was a crude preparation from *E. coli* and contained ribonucleases.

4. Durability of Armored RNA™ compared to naked RNA

One advantage of "ARMORED RNA" is that rather than adding the "ARMORED RNA" standard to the lysis solution prior to the lysis procedure, the "ARMORED RNA" standard may be added to the plasma or serum sample prior to RNA isolation, thus minimizing pipetting error in the assay. "ARMORED RNA" withstands plasma/serum nucleases very well compared to naked RNA.

RNA purified from AR-2 (about 5000 RNA molecules), and intact AR-2 (500 QS RNA equivalents) were each added to 0.2 ml of normal human serum and incubated, 21° C. for 0 sec, 15 sec, 30 sec, 1 min, 5 min, 15 min, 1 h, and 4 h. The incubations were stopped by the addition of 4M guandinine thiocyanate, and 1% Sarkosyl solution and the RNA was extracted from the serum according to the method of Chomczynski (1987). Fifty microliters of a purified RNA preparation was amplified by "RT-PCR" for 26 cycles using the SK431/SK462 primer pair. The "PCR" products were quantified with a solid phase ELISA system (Mulder, 1994).

Figure 2:
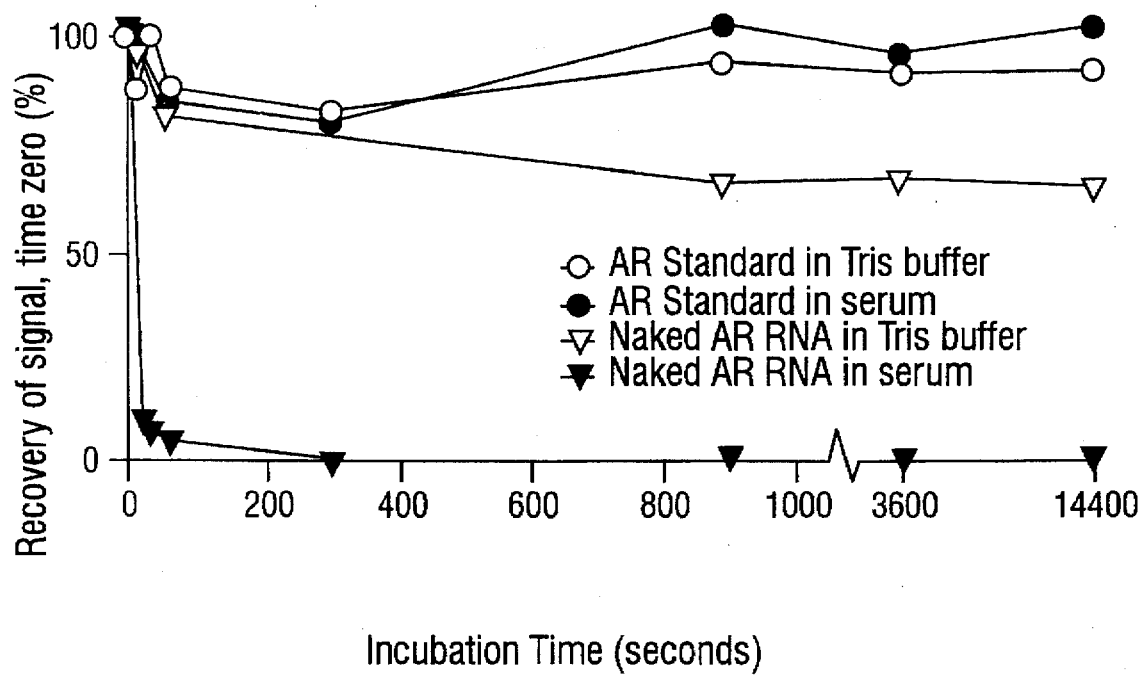
FIG. 2. The effect of incubating intact AR-2 standards or naked AR-2 RNA in human serum. A defined amount of RNA either encapsidated as AR-2 (500 RNA equivalents), or as naked RNA isolated from AR-2 (5000 RNA equivalents) were incubated with human serum for increasing periods at room temperature (21° C.). As controls, the naked AR-2 RNA and the intact AR-2 standard were both incubated in parallel in Tris-buffer. Percent recovery was calculated as the $OD_{450}X$ dilution factor (DF) of the samples at time zero divided by $OD_{450}X$ DF at the end of each incubation multiplied by 100.

The AR-2 generated the same signal over the full time course while the signal from the purified RNA from the AR-2 disappeared almost immediately (FIG. 2). Clearly, the RNA in AR-2 was protected against plasma ribonucleases compared to the naked RNA.

EXAMPLE II

Use of Armored RNA™ Standards in Assay Kits

1. Use of ARMORED RNA Standard in the "AMPLICOR" HIV Monitor Assay

To perform the "AMPLICOR" HIV Monitor assay, a quantitative RNA standard of a known quantity is added to the patient's plasma sample and then RNA is isolated from the plasma. "RT-PCR" is performed on the RNA such that the standard and the HIV RNA are co-amplified using a single primer set. Both PCR products are measured and then the concentration of the HIV RNA is calculated using the signal obtained from the quantitative standard.

The "ARMORED RNA" standard containing the QS sequence (AR-2) is used in the "AMPLICOR" HIV Monitor test as follows. A known quantity of AR2(~10 µl) is added to 0.2 ml of sample plasma. 0.6 ml of Lysis Reagent is added to the plasma sample containing the AR-2. The sample is mixed by vortexing 3–5 seconds and then incubated at room temperature 10 minutes. 0.8 ml of isopropanol is added to the sample tube and the sample is mixed by vortexing 3 to 5 seconds. The sample is centrifuged at maximum speed (~16,000×g) for 15 minutes. The supernatant is dicarded without disrupting the pellet. 1 ml of 70% ethanol is added and the sample is vortexed 3 to 5 second, followed by centrifugation for 5 minutes at -16,000 ×g.

The pellet is resuspended in 0.4 ml of Specimen Diluent. 50 µl of the extracted sample is added to a MicroAmp tube containing the Master Mix and "RT-PCR" is performed using the Tth Polymerase.

After amplification, 0.1 ml of Denaturation solution is added to the amplicons. 0.1 ml of Hybridization Solution is added to each well of the Microwell Plate (MWP) used for detection of the amplicons. 25 µl of the denatured amplicon is added to the first well and then a series of 1:5 dilutions are performed using 25 µl in the next 4 consecutive wells such that there are dilutions of 1:5, 1:25, 1:125, 1:625 and 1:3125 for the detection of the HIV amplicon. Dilutions of 1:5 and 1:25 are made in the appropriate wells for the detection of the QS amplicon. The MWP is incubated for 1 hour at 37° C.

The wells are washed 5 times with Working Wash Solution and then 0.1 ml of AV-HRP is added to each well and the MWP is incubated 15 minutes, 37° C.

The MWP is washed 5 times with the Working Wash Solution. 0.1 ml of the Working Substrate is added to each well and the MWP is incubated 10 minutes, in the dark at room temperature. Add 0.1 ml of Stop Solution to each well and the optical density is measured at 450 nm. The concentration of the HIV in the plasma is calculated based on the signal obtained from the known concentration of the QS standard added to the patient plasma.

Besides using "ARMORED RNA" as a substitute for the naked QS RNA standard in the HIV Monitor assay, "ARMORED RNA" may also be used as a positive control in the assay. A wild-type sequence of HIV compatible with the HIV Monitor test could be packaged in "ARMORED RNA" such that it behaves as if it were a wild-type HIV. In this embodiment, an "ARMORED RNA" HIV Positive control is added to normal plasma at a known quantity and is then processed as if it were a patient sample except that the user would expect to obtain a certain pre-determined value in the assay. This standard would be used to demonstrate to the user that the assay was functioning properly.

2. Modified "AMPLICOR" HIV Monitor test procedure well suited to "ARMORED RNA"

To increase the sensitivity of detection for HIV in the "AMPLICOR" assay, a procedure was developed in which the HIV virions are pelleted by high speed centrifugation from the plasma sample. Thus, 1 ml of plasma can now be assayed instead of the conventional 0.2 ml which the assay has used. This procedure should theoretically increase the sensitivity 5 fold.

In this new procedure, the naked QS RNA would not be an optimal standard. It cannot be added to a plasma sample due the ribonucleases in the plasma which would degrade it and the naked QS RNA would not pellet by centrifugation with the HIV virions. Thus, when the plasma is removed after centrifugation, there is no control for loss of the HIV pellet. "ARMORED RNA" may be added to the plasma prior to centrifugation. It should pellet similarly to the HIV. Thus any loss of the pellet would be reflected in an equal loss in signal obtained from the "ARMORED RNA" standard. Importantly, the "ARMORED RNA" standards would allow the centrifugation protocol to be practiced as a quantitative assay.

3. Use of "ARMORED RNA" in Other Kits

Of course, the invention is not limited to a single, exemplary assay. There are other RNA based assays for HIV including: NASBA which is based on isothermal amplification (van Gemen, 1994; sold by Organon Teknika); the branched DNA assay developed by Chiron; an assay by DiGene in which an antibody recognizes a DNA/RNA duplex; and transcription mediated amplification, a technology similar to NASBA developed by Gen-Probe. For each of these assays, one skilled in the art can construct an "ARMORED RNA" standard containing appropriate sequence(s) to function appropriately as a quantitative standard.

The HIV NASBA assay uses three different quantitative RNA standards. The sequences of these standards are available in van Gemen (1994). Each of these NASBA standards could be cloned into pAR-1 in the same manner that the QS sequence was cloned into pAR-1 to produce "ARMORED RNA" standards for the NASBA assay. "RT-PCR" may be used to amplify each of the standards for cloning into pAR-1 or they could be synthesized chemically.

The branched DNA assay by Chiron uses a single stranded DNA as the RNA standard. It encodes the gag and pol genes of HIV strain SF2. The sequence for this strain of HIV is available from GenBank, Accession number K02007. This HIV standard sequence is ~3 kb and may be too long for its full length to be packaged using pAR-1 as the vector for "ARMORED RNA" synthesis. It may be necessary to use a different construct which may permit longer sequences to be packaged. One such "ARMORED RNA" construct would be comprised of Maturase protein, Coat Protein and Maturase Binding Sites and the HIV sequence encoding gag and pol. The Maturase would be encoded on another plasmid provided in trans. In this construct, the deletion of the Maturase Coding sequence from the reRNA may permit for the packaging of more non-bacteriophage sequence.

EXAMPLE III

Use of "ARMORED RNA" in a HIV Gel-Based Assay

An "ARMORED RNA" may be used as an external quantitative standard. A fragment of the HIV genome such as that region bounded by the SK431 and SK462 primers or some other region such as sequence encoding the pol gene can be cloned into the pAR-1 backbone. This construct can be used to synthesize "ARMORED RNA" in which the entire length of the cloned HIV fragment is wild-type HIV sequence. Such an assay does not need a unique capture sequence since each amplicon is detected on an acrylamide or agarose gel either by ethidium bromide staining or by labeling the "PCR" product with $^{32}P$ incorporation and autoradiography. A standard curve is generated by introducing known amounts of the HIV sequence into the "RT-PCR" assay and then quantifying the amount of product generated on a gel. Actual copy numbers for test samples may then be derived using the standard curve. The "ARMORED RNA" is calibrated and used in "RT-PCR" reactions as if it were actual HIV. The "PCR" fragments may be fractionated either by agarose or acrylamide gel electrophoresis and quantified by ethidium staining or radioactivity. Standard curves may be generated by processing plasma containing different concentrations of the "ARMORED RNA". The standard curve may then be used to calculate the tilers of patient samples by interpolation.

EXAMPLE IV

Use of "ARMORED RNA" as a Non-Infectious Standard

"ARMORED RNA" may be used as non-infectious proficiency standard (a certified and well characterized plasma, serum or urine based product designed for the validation of the accuracy of the instrumentation and methods of an assay) or as positive controls. Gene fragments of a standard HIV strain are cloned into the "ARMORED RNA" recombinant plasmid to produce a family of "ARMORED RNA"- HIV standards. These include the pol and gag genes, which are well conserved in HIV. The inventors envision AR-gag, AR-pol and AR-gag/pol RNA standards. These "ARMORED RNA" standards are quantified precisely and then can be used as external quantitative standards for "RT-PCR" or other amplification techniques. The "ARMORED RNA" may be added directly to plasma and used as such, or the AR-HIV RNA may be extracted from the purified "ARMORED RNA" in a standard salt buffer such as PBS or Tris:NaCl.

EXAMPLE V

An "ARMORED RNA" Standard Used in an HCV Assay

"ARMORED RNA" technology will be useful in creating RNA standards for viruses that are difficult or hazardous to culture. For example, hepatitis C virus (HCV) cannot be reliably grown in tissue culture, whereas an "ARMORED RNA" standard for HCV can be made. HCV isolates can be classified into 6 distinct genotypes based on the nucleotide sequence variation in the core gene region or the NS5 region (Simmonds, 1994). Genotype-specific "ARMORED RNA" standards can be constructed to serve as controls in assays designed to identify specific HCV genotypes and HCV subtypes such as 1a, 1b, 2a, 2b, 2c, 3, 4a, 4b, 5a, and 6a. Genotyping strategies have been based on sequencing, RFLP analysis, "PCR"-based assays with type-specific primers, and a line probe assay (van Doorn, 1994). For example, the latter assay involves the differential capture of a 244 basepair product that is generated from primers at positions 56 through 299 of the HCV genome. The amplicon used to identify each of these strains is short enough that it is straightforward to chemically synthesize the DNA fragments to be cloned into pAR-1 and thus circumvent the need to handle infectious material in order to clone these genotype sequences. Protected recombinant RNA from human serum samples could be constructed using primers KY80 (5'GCAGAAAGCGTCTAGCCATGGCGT) (KY80-SEQ ID NO:7) and KY78 (5'CTCGCAAGCACCCTATCAGG-CAGT) (KY78-SEQ ID NO:8). By using samples with defined genotypes, genotype-specific recombinant standards could be constructed. "ARMORED RNA" standards for HCV may be constructed using a strategy similar to the one for the HIV standard. These RNA standards may be used either as positive controls for strain typing or quantitative RNA standards.

For strain typing, the primers KY78 and KY80 may be used to synthesize DNA fragments by "RT-PCR" from different HCV strains. These strain specific DNA fragments may be cloned into pAR-1 such that RNA encoding strain specific HCV is packaged as "ARMORED RNA". As well, strain specific sequences have also been documented for HCV between positions 56 to 299 of the HCV genome. It is possible to chemically synthesize these sequences and clone them directly into pAR-1 for packaging. This method would circumvent the need to handle infectious HCV. Thus, in the differential capture assay, each strain specific "PCR" product of HCV would hybridize to a unique capture probe immobilized to the bottom of a plastic well.

To create a quantitative HCV "ARMORED RNA" standard, the amplicon produced by the KY78 and KY80 primers could be modified by substituting in the same capture sequence used in the QS sequence for HIV or some other 25 to 30 base pair region within this amplicon may be randomized so that it can be differentiated from the wild-type amplicon. The substitution may be performed by one skilled in the art by "PCR". As in the "AMPLICOR" HIV assay, the HCV quantitative standard would be co-amplified with the wild-type RNA. The HCV "ARMORED RNA" standard would be added to the sample plasma prior to the RNA isolation step.

EXAMPLE VI

Collection Tubes Containing Pre-Determined Quantity of "ARMORED RNA"

Owing to the durability and stability of "ARMORED RNA", it may be aliquoted into blood collection vessels or other fluid collection vessels in a pre-determined quantity. The "ARMORED RNA" may then be freeze dried for long term storage at room temperature or left in buffered salt solution and stored at 4° C. or even room temperature (~21° C.). At the time of use, blood is drawn into the collection tube with the "ARMORED RNA" standard. The blood sample is inverted many times to thoroughly mix the "ARMORED RNA" standard into the sample. The blood may be stored as usual until it is subjected to the quantitative assay. This strategy precludes the need to add an RNA standard to the plasma sample prior to the RNA isolation from plasma. It would control for the partitioning of the viruses between the blood cells and the plasma or serum fractions.

Further, multiple "ARMORED RNA" standards may be included in the collection tube such as an HIV and an HCV standard so that the quantification for one or both pathogens may be performed.

EXAMPLE VII

Use of "ARMORED RNA" in Veterinary Diagnostics

Domestic animals are often infected with RNA viruses. For cats, retroviruses represent the largest cause of premature death other than automobile accidents. Up to one-third of the cats exposed, are infected with Feline Immunodeficiency Virus (FIV) and Feline Leukemia Virus (FeLV) (Essex, 1995), similar to their human counterparts, HIV and human T cell lymphotropic virus-type 1 (HTLV). One skilled in the art could construct "ARMORED RNA" standards for FIV and FTLV, similar to the AR-2 standard described for HIV. These standards may be used for quantificafion or as positive controls in FIV and FeLV diagnosis by RT-PCR™.

EXAMPLE VIII

Use of Double Stranded RNA Bacteriophage

Bacteriophage φ6 is a double stranded RNA bacteriophage in which it is possible to package in vitro, non-bacteriophage RNA to produce viable, genetically stable bacteriophage (Qiao, 1995). It has been demonstrated that the RNA in these bacteriophage are protected from ribonucleases. One skilled in the art may produce recombinants containing a standard RNA sequence so that the recombinant bacteriophage φ6 may act as quantitative standards for human infectious, double stranded RNA viruses such Rota Virus and Vesicular Stomatitis Virus. It is possible following the teachings of this specification and the art to develop a packaging system with bacteriophage φ6 whereby the packaged material is not viable/infectious, similar to the "ARMORED RNA" standards.

A double stranded non-infectious RNA bacteriophage may have applications as a therapeutic. Double stranded RNA is known to stimulate cells to produce important immunomodulators which act as anti-viral agents such as interferon (Stiehm, 1982).

EXAMPLE IX

Quantification of a Cellular mRNA

One skilled in the art can use an "ARMORED RNA" standard for the quantification of an mRNA expressed by a cell. In studies to determine the induction or repression of specific mRNAs over a period of time, an equal number of cells could be harvested at each time point before and after the cells had been exposed to the treatment under investigation. The "ARMORED RNA" standard would be added in a known quantity to each time point prior to the purification of the RNA from the cells. The "ARMORED RNA" standard could then be used to quantify the mount of a target mRNA such as a cytokine, a cell cycle gene or an oncogene. The "ARMORED RNA" standard would be constructed containing the same primer pair binding sites as the target gene. The "ARMORED RNA" standard could be differentiated from the wild type "RT-PCR" product by altering the sequence between the primers pairs using one of the methods discussed above such as incorporating a restriction site or a deletion. One skilled in the art can produce amplicons which have insertions, deletions or substitutions as compared to the wild-type sequence. There are several different methods available for site-directed mutagenesis, each of which involve oligonucleotides which encode the desired sequence of the standard.

Standards containing deletions, insertions and restriction sites are often preferred for gel based assays because they are easily differentiated from the wild-type amplicon by fractionation on an agarose or acrylamide gel. For each of these standards, a size difference of about 10% is often used. "PCR" may be used to generate any of these standard sequences. To generate a deletion mutant, an oligonucleotide is synthesized which contains primer sequences as well as other amplicon sequence. The amplicon sequence and the primer sequence flank the sequence in the wild-type sequence which is to be deleted. When this oligonucleotide hybridizes to the wild-type, the sequence to be deleted is looped out and is not incorporated into the new DNA strand during polymerase extension. One skilled in the art may use similar strategy to create insertions and substitutions whereby one of the primers in a "PCR" reaction contains the desired mutation. Two such strategies are discussed in detail in Schneeberger (1996) and Hughes (1996).

EXAMPLE X

Preparation of "ARMORED RNA" Standards for Commercial Use

It is important that the "ARMORED RNA" standard is free of any host DNA or RNA which may affect quantification by "RT-PCR". To produce a homogenous lot of an "ARMORED RNA" standard, a crude extract would be prepared from the culture supernatant after a 16 h induction of the E. coil transformants (see EXAMPLE I). This preparation is contaminated with the genomic DNA from E. coli. Contaminating RNA and DNA may be removed by adding RNase and DNase to the crude extract.

Traditionally, MS2 bacteriophage are purified by a CsCl gradient. They band tightly at a concentration of 1.45 g/cc (Pickett, 1993). "ARMORED RNA" may be purified by using a CsCl gradient procedure similar to the MS2 bacteriophage. After centrifugation, the "ARMORED RNA" band is pulled and then dialyzed against a salt buffer such 100 mM NaCl:50 mM Tris (pH 7.5) or PBS. "ARMORED RNA" may be quantified by obtaining an $OD_{260}$ and an $OD_{280}$ which are used to measure nucleic acid and protein concentrations, respectively. After a stock of "ARMORED RNA" has been made, it may be calibrated against a naked RNA containing the same amplicon. For example, "ARMORED RNA" standards may be calibrated against the naked QS RNA standard.

The nuclease treated crude extract of "ARMORED RNA" may be also purified by gel exclusion chromatography, using a resin such as Sephacryl S-200 (Pharmacia) (Heisenberg, 1966). Due to the large size of the "ARMORED RNA", they will run in the void volume while other protein and nucleic acid components will be retarded. "ARMORED RNA" in the void volume may be calibrated as above. It will be advantageous to couple several purification procedures to ensure that the "ARMORED RNA" is completely homogenous.

Large scale production of "ARMORED RNA" may be performed as follows. A 100 ml inoculum of E. coli harboring the pAR construct is grown to mid-log phase in $Cb_{25}$-LB medium. This inoculum is used to inoculate 1,000 ml of 1 mM IPTG- $Cb_{25}$-LB medium. The cells are incubated 16 h, 200 rpm, 37° C. One ml of lysozyme (50 mg per ml) is added to the culture and incubated 37° C., 1 h, 200 rpm. The culture is pelleted by centrifugation. The supernatant contains "ARMORED RNA" particles and E. coli genomic and plasmid DNA. Contaminating RNA and DNA is degraded by adding $CaCl_2$ to the supernatant to 10 mM and the supernatant is then incubated with Micrococcal Nuclease (30 units/ml), 37° C., 1 h, 200 rpm. EDTA is added to 25 mM to chelate the $CaCl_2$ and stop the nuclease activity. The AR particles are precipitated with 50% Ammonium Sulfate, 4° C., 2 h. The precipitate is pelleted by centrifugation. The pellet is resuspended in 100 mM NaCl:1 mM EDTA: 10 mM Tris (pH 7.5) (TSE buffer). 0.6 g of CsCl is added to every gram of AR2 solution. The CsCl is dissolved and transferred to a heat sealed ultracentrifugation robe for the 50.2 Ti rotor (Beckmann). The CsCl gradient is centrifuged at 45,000 rpm, 20 h, 21° C. The AR particles band about the middle of the centrifuge robe. The CsCl band is pulled with a needle and syringe, about 5 ml. The AR2 particles are finally passed over an Sephacryl S-200 resin in TSE buffer. The particles elute in the void volume. The number of AR2 particles may be determined using the extinction coefficient of 1 $OD_{260}=8$ mg/ml of MS2 bacteriophage and the molecular weight is $3\times10^6$. Based on this procedure, approximately $1\times10^{16}$ AR particles can be purified from one liter of culture.

Electron microscopy may be used to count the "ARMORED RNA" directly. This method has been used for quantifying HIV (Lu, 1993).

After purification, the "ARMORED RNA" may be stored at 4° C. or at room temperature. A biocide may be added to prevent bacterial or fungal growth in the standards. The "ARMORED RNA" is diluted to concentrations which are convenient for quantification.

While the compositions and methods of this invention have been described in terms of preferred embodiments, it will be apparent to those of skill in the art that variations may be applied to the compositions, methods and in the steps or in the sequence of steps of the methods described herein without departing from the concept, spirit and scope of the invention. More specifically, it will be apparent that certain agents which are both chemically and physically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

Argetsinger and Gussin, "Intact ribonucleic acid from defective particles of bacteriophage R17," *J. Mol. Biol.*, 21:421–434, 1966.

Birnboim, "A rapid alkaline extraction method for the isolation of plasmid DNA," *Methods of Enzymology*, 100:243–255, 1983.

Chomczynski and Sacchi, "Single-step method of RNA isolation by acid guanidinium thiocynanate-phenol-chloroform extraction," *Anal. Biochem.*, 162:156–159, 1987.

Collins, Zayati, Detmer, Daly, Kolberg, Cha, Irvine, Tucker, and Urdea, "Preparation and characterization of RNA standards for use in quantitative branched DNA hybridization assays," *Anal. Biochem.*, 226:120–129, 1995.

Essex, "The HIV-1 vaccine dilemma: lessons from the cat," *J. NIH Res.*, 7:37–42, 1995.

Hughes and Andrews, "Creation of deletion, insertion and substitution mutations using a single pair of primers and PCR," *BioTechniques*, 20:188–196, 1996.

Lu and Andrieu, "Use of the human immunodeficiency virus virion as a universal standard for viral RNA quantification by reverse transcription-linked polymerase chain reaction," *J. Infect. Dis.*, 167:1498–1499, 1993.

Mulder, McKinney, Christopherson, Sninsky, Greenfield, and Kwok, "Rapid and simple PCR™ assay for quantitation of human immunodeficiency virus type 1 RNA in plasma: application to acute retroviral infection," *J. Clin. Microbiol.*, 32:292–300, 1994.

Pachl, Todd, Kern, Sheridan, Fong, Stempien, Hoo, Besemer, Yeghiazarian, Irvin, Kolberg, Kokka, Neuwald, Urdea, "Rapid and precise quantification of HIV-1 RNA in plasma using a branched DNA signal amplification assay," *J. Acquir. Immune Defic. Syndr.* 8:446–454, 1995.

Piatak, Jr., Luk, Williams, and Lifson, "Quantitative competitive polymerase chain reaction for accurate quantitation of HIV DNA and RNA," *BioTechniques*, 14:70–79, 1993.

Pickett and Peabody, "Encapsidation of heterologous RNAs by bacteriophage MS2 Coat Protein," *Nucl. Acids Res.*, 21:4621–4626, 1993.

Qiao, Qiao, and Mindich, "Interference with bacteriophage φ6 genomic RNA packaging by hairpin structures," *J. Virol.*, 69:502–5505, 1995.

Schneeberger and Zeillenger, "PCR-mediated synthesis of exogenous competitors for quantitative RT-PCR," *BioTechniques*, 20:360–362, 1996.

Shaklee, "Negative-strand RNA replication by Q-beta and MS2 positive-strand RNA bacteriophage Replicases," *Virology*, 178:340–343, 1990.

Shiba and Suzuki, "Localization of A protein in the RNA-A protein complex of RNA bacteriophage MS2," *Biochem. Biophys. Acta*, 654:249–255, 1981.

Simmonds et al., "A proposed system for the nomenclature of hepatitis C virus genotypes," *Hepatology*, 19:1321–1324, 1994.

Stiehm et al., "Interferon: immunobiology and clinical significance," *Ann. Intern. Med*, 96:80, 1982.

Stockley, Stonehouse, and Valegård, "Molecular mechanism of RNA bacteriophage morphogenesis," *Int. J. Biochem.*, 26:1249–1260, 1994.

van Doorn, Kleter, Stuyver, Maertens, Brouwer, Schalm, Heijtink, and Quint, "Analysis of hepatitis C virus genotypes by a line probe assay and correlation with antibody profiles," *J. Hepatology*, 21: 122–129, 1994.

van Gemen, van Beuningen, Nabbe, van Strijp, Jurriaans, Lens, and Kievits, "A one-tube quantitative HIV-1 RNA NASBA nucleic acid amplification assay using electrochemiluminescent (ECL) labelled probes," *J. Virol. Methods*, 49:157–168, 1994.

Witherell, Gott, and Uhlenbeck, "Specific interaction between RNA bacteriophage Coat Proteins and RNA," *Proc. Nuc. Acid Res. Molec. Biol.*, 40:185–220, 1991.

---

What is claimed is:

1. An RNA detection and/or quantification standard comprising a recombinant RNA segment encapsidated in bacteriophage viral Coat Protein, wherein said recombinant RNA segment comprises a bacteriophage sequence and a non-bacteriophage sequence, and wherein the RNA standard is resistant to ribonuclease.

2. The RNA detection and/or quantification standard of claim 1, wherein the bacteriophage viral coat protein is a modified bacteriophage viral coat protein.

3. The RNA detection and/or quantification standard of claim 1, wherein the bacteriophage viral coat protein is of an E. coli bacteriophage of genetic subclass A.

4. The RNA detection and/or quantification standard of claim 1, wherein the bacteriophage viral coat protein is of an E. coli bacteriophage of serological group I.

5. The RNA detection and/or quantification standard of claim 1, wherein the bacteriophage viral coat protein is of an MS2/R17 bacteriophage.

6. The RNA detection and/or quantification standard of claim 1, wherein the non-bacteriophage sequence is a vital sequence.

7. The RNA detection and/or quantification standard of claim 1, wherein the bacteriophage sequence is a sequence from an E. coli bacteriophage of genetic subclass A.

8. The RNA detection and/or quantification standard of claim 1, wherein the bacteriophage sequence is a sequence from an E. coli bacteriophage of serological group I.

9. The RNA detection and/or quantification standard of claim 1, wherein the bacteriophage sequence is a sequence from an MS2/R17 bacteriophage.

10. The RNA detection and/or quantification standard of claim 1, wherein the recombinant RNA segment comprises at least two viral Maturase binding sites.

11. The RNA detection and/or quantification standard of claim 1, wherein the recombinant RNA segment comprises at least two Operator sequences.

12. The RNA detection and/or quantification standard of claim 1, wherein the recombinant RNA segment comprises an Operator sequence and a viral coat protein sequence.

13. The RNA detection and/or quantification standard of claim 1, wherein the recombinant RNA segment comprises an Operator sequence, a sequence coding a viral Maturase protein and a non-bacteriophage sequence.

14. The RNA detection and/or quantification standard of claim 1, wherein the recombinant RNA segment comprises an Operator sequence, a sequence coding a viral Maturase protein and a sequence coding a viral coat protein and a non-bacteriophage sequence.

15. The RNA detection and/or quantification standard of claim 1, wherein the recombinant RNA segment comprises an Operator sequence, at least two viral Maturase binding sites, a sequence coding a viral Maturase protein, a sequence coding a viral coat protein and a non-bacteriophage sequence.

16. The RNA detection and/or quantification standard of claim 1, wherein the recombinant RNA segment comprises an Operator sequence, at least two viral Maturase binding sites, a sequence coding a viral Maturase protein, a sequence coding a viral coat protein and a non-bacteriophage sequence, and a sequence coding a Replicase protein.

17. The RNA detection and/or quantification standard of claim 1, wherein the bacteriophage viral coat protein is of an E. coli bacteriophage.

18. The RNA detection and/or quantification standard of claim 1, further comprising a viral Maturase protein.

19. The RNA detection and/or quantification standard of claim 18, wherein the viral Maturase protein is a modified viral Maturase protein.

20. The RNA detection and/or quantification standard of claim 19, wherein the recombinant RNA segment comprises an Operator coding sequence and a viral Maturase protein binding site.

21. The RNA detection and/or quantification standard of claim 20, wherein the Operator coding sequence is a modified Operator coding sequence.

22. The RNA detection and/or quantification standard of claim 20, wherein the recombinant RNA segment further comprises a viral Maturase protein coding sequence.

23. The RNA detection and/or quantification standard of claim 20, wherein the recombinant RNA segment further comprises a viral coat protein coding sequence.

24. The RNA detection and/or quantification standard of claim 23, wherein the viral Coat Protein coding sequence codes for a bacteriophage viral coat protein.

25. The RNA detection and/or quantification standard of claim 24, wherein the bacteriophage viral Coat Protein is a modified bacteriophage viral coat protein.

26. The RNA detection and/or quantification standard of claim 1, wherein the non-bacteriophage sequence is a standard.

27. The RNA detection and/or quantification standard of claim 26, wherein the non-bacteriophage sequence is a diagnostic standard.

28. The RNA detection and/or quantification standard of claim 27, wherein the non-bacteriophage sequence is an HIV-1, HIV-2, HCV, HTLV-1, HTLV-2, hepatitis G, an enterovirus, or blood-borne pathogen standard.

29. The RNA detection and/or quantification standard of claim 27, wherein the non-bacteriophage sequence is an HIV-1, HIV-2, or HCV standard.

30. The RNA detection and/or quantification standard of claim 27, wherein the non-bacteriophage sequence is an HIV-1 standard.

31. The RNA detection and/or quantification standard of claim 30, wherein the non-bacteriophage sequence is an HIV-1 standard and comprises a modified HIV-1 sequence.

32. The RNA detection and/or quantification standard of claim 1, wherein the recombinant RNA segment comprises a sequence coding a Replicase protein.

33. The RNA detection and/or quantification standard of claim 32, wherein the sequence coding the Replicase protein codes a modified Replicase protein that is not active.

34. The RNA detection and/or quantification standard of claim 1, wherein the RNA detection and/or quantification standard is an HIV-1, HIV-2, HCV, HTLV-1, HTLV-2, hepatitis G, an enterovirus, or blood-borne pathogen RNA detection and/or quantification standard.

35. The RNA detection and/or quantification standard of claim 34, wherein the RNA detection and/or quantification standard is an HIV-1 or HIV-2 RNA detection and/or quantification standard.

36. A recombinant RNA segment comprising an Operator coding sequence, a viral Maturase protein binding site, and a non-bacteriophage sequence.

37. The recombinant RNA segment of claim 36, further comprises a viral Maturase protein coding sequence.

38. The recombinant RNA segment of claim 36, wherein the viral coat protein coding sequence codes for a bacteriophage viral coat protein.

39. The recombinant RNA segment of claim 36, wherein the non-bacteriophage sequence is a viral sequence.

40. The recombinant RNA segment of claim 36, wherein the non-bacteriophage sequence is an HIV-1, HIV-2, HCV, HTLV-1, HTLV-2, hepatitis G, an enterovirus, or blood-borne pathogen standard.

41. The recombinant RNA segment of claim 36, further comprising at least two viral Maturase binding sites.

42. The recombinant RNA segment of claim 36, further comprising at least two Operator sequences.

43. A DNA vector for synthesis of an RNA detection and/or quantification standard comprising a recombinant RNA segment encapsidated in bacteriophage viral Coat Protein, wherein said recombinant RNA segment comprises a bacteriophage sequence and a non-bacteriophage sequence, and wherein the RNA detection and/or quantification standard is resistant to ribonuclease.

44. The vector of claim 45, further comprising a sequence coding a viral coat protein gene.

45. The vector of claim 43, wherein the vector comprises a sequence coding an Operator sequence, a sequence coding a viral Maturase binding site, and a multiple cloning site.

46. The vector of claim 45, further comprising a sequence coding a viral Maturase protein.

47. The vector of claim 45, further comprising a DNA sequence coding a non-bacteriophage sequence in the multiple cloning site.

48. The vector of claim 47, wherein the non-bacteriophage sequence is a viral non-bacteriophage sequence.

49. The method of claim 47, wherein the recombinant RNA segment comprises an Operator sequence, a sequence coding a viral Maturase protein, and a non-bacteriophage sequence.

50. A collection tube containing an RNA detection and/or quantification standard comprising a recombinant RNA segment encapsidated in bacteriophage viral Coat Protein, wherein said recombinant RNA segment comprises a bacteriophage sequence and a non-bacteriophage sequence, and wherein the RNA detection and/or quantification standard is resistant to ribonuclease.

51. A method of assaying for the presence of an RNA of diagnostic value comprising:

1) obtaining a sample to be assayed;
2) obtaining an RNA detection and/or quantification standard comprising a recombinant nucleic acid encapsidated in bacteriophage viral coat protein, wherein the RNA detection and/or quantification standard is resistant to ribonuclease;
3) admixing the sample with the RNA detection and/or quantification standard;
4) isolating RNA from the admixture; and
5) assaying for the presence of the RNA of diagnostic value.

52. The method of claim 51, wherein the recombinant RNA segment comprises an Operator sequence and a viral coat protein sequence.

53. The method of claim 51, wherein the recombinant RNA segment comprises an Operator sequence, a sequence coding a viral Maturase protein, a sequence coding a bacteriophage viral coat protein and a non-bacteriophage sequence.

54. The method of claim 51, wherein the recombinant RNA segment comprises an Operator sequence, at least two viral Maturase binding sites, a sequence coding a bacteriophage viral Maturase protein, a sequence coding a viral coat protein and a non-bacteriophage sequence.

55. The method of claim 51, wherein the recombinant RNA segment comprises an Operator sequence, at least two viral Maturase binding sites, a sequence coding a viral Maturase protein, a sequence coding a bacteriophage viral coat protein, a non-bacteriophage sequence, and a sequence coding a Replicase protein.

56. A method of making an RNA detection and/or quantification standard comprising a recombinant RNA segment encapsidated in bacteriophage viral Coat Protein, wherein said recombinant RNA segment comprises a bacteriophage sequence and a non-bacteriophage sequence, and wherein the RNA detection and/or quantification standard is resistant to ribonuclease, comprising:

1) obtaining a vector comprising a DNA sequence coding a recombinant RNA segment comprising a sequence coding an Operator and a non-bacteriophage sequence;
2) transfecting the vector into a cell;
3) obtaining a DNA segment coding a bacteriophage viral Coat Protein and transfecting the nucleic acid segment coding the bacteriophage viral Coat Protein into the cell; and
4) culturing the cell under conditions allowing for transcription of the recombinant RNA segment, expression of the bacteriophage viral Coat Protein, and encapsidation of the recombinant RNA segment in bacteriophage viral Coat Protein such that the RNA detection and/or quantification standard is resistant to ribonuclease.

57. A method of making an RNA detection and/or quantification standard in vivo comprising:

1) obtaining a vector comprising a DNA sequence coding a recombinant RNA sequence;
2) transfecting the vector into a cell;
3) obtaining a DNA segment coding a bacteriophage viral Coat Protein;
4) transfecting the DNA segment coding the bacteriophage viral Coat Protein into the cell; and
5) culturing the cell under conditions allowing for transcription of the recombinant RNA segment, expression of the bacteriophage viral Coat Protein, and encapsidation of the recombinant RNA segment in bacteriophage viral Coat Protein such that the encapsidated RNA is resistant to ribonuclease.

* * * * *

UNITED STATES PATENT AND TRADEMARK OFFICE
CERTIFICATE OF CORRECTION

PATENT NO. : 5,677,124

DATED : October 14, 1997

INVENTOR(S) : DuBois et al.

It is certified that error appears in the above-identified patent and that said Letters Patent is hereby corrected as shown below:

In claim 1, column 31, line 52, delete "Coat Protein" and insert therefor --coat protein--.
In claim 24, column 33, line 47, delete "Coat Protein" and insert therefor --coat protein--.
In claim 25 column 33, line 50, delete "Coat Protein" and insert therefor --coat protein--.
In claim 43, column 34, lines 39 and 40, delete "Coat Protein" and insert --coat protein-- therefor.
In claim 49, column 34, line 57, delete "47" and insert --51-- therefor.
In claim 50, column 34, line 63, delete "Coat Protein" and insert --coat protein-- therefor.
In claim 56, column 35, line 36, delete "Coat Protein" and insert --coat protein-- therefor.
In claim 56, column 36, line 9, delete "Coat Protein" and insert --coat protein-- therefor.
In claim 56, column 36, line 10, delete "Coat Protein" and insert --coat protein-- therefor.
In claim 56, column 36, line 15, delete "Coat Protein" and insert --coat protein-- therefor.
In claim 56, column 36, line 17, delete "Coat Protein" and insert --coat protein-- therefor.

UNITED STATES PATENT AND TRADEMARK OFFICE
CERTIFICATE OF CORRECTION

PATENT NO.   :   5,677,124

DATED        :   October 14, 1997

INVENTOR(S)  :   DuBois et al.

It is certified that error appears in the above-identified patent and that said Letters Patent is hereby corrected as shown below:

In claim 57, column 36, line 22, after 'RNA', insert --segment comprising a sequence coding an operator sequence and a non-bacteriophage--.
In claim 57, column 36, line 26, delete "Coat Protein" and insert --coat protein-- therefor.
In claim 57, column 36, line 28, delete "Coat Protein" and insert --coat protein-- therefor.
In claim 57, column 36, line 31, delete "Coat Protein" and insert --coat protein--.
In claim 57, column 36, line 33, delete "Coat Protein" and insert --coat protein-- therefor.

Signed and Sealed this

Twenty-fourth Day of February, 1998

Attest:

BRUCE LEHMAN

*Attesting Officer*    *Commissioner of Patents and Trademarks*